US012788693B2

(12) United States Patent
Yokogi et al.

(10) Patent No.: US 12,788,693 B2
(45) **Date of Patent: *Nov. 10, 2026**

(54) PERSONAL CARE PRODUCT CUSTOMIZED BY DISCRETE PARTICLES AND METHOD OF APPLY THEREOF

(71) Applicant: The Procter & Gamble Company, Cincinnati, OH (US)

(72) Inventors: Junichi Yokogi, Singapore (SG); Andrew Weatherston, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 336 days.

This patent is subject to a terminal disclaimer.

(21) Appl. No.: 18/422,155

(22) Filed: Jan. 25, 2024

(65) Prior Publication Data

US 2024/0156700 A1 May 16, 2024

Related U.S. Application Data

(63) Continuation of application No. 16/595,755, filed on Oct. 8, 2019, now Pat. No. 11,931,441.

(60) Provisional application No. 62/743,562, filed on Oct. 10, 2018.

(51) Int. Cl.

| | |
|---|---|
| ***A61K 8/36*** | (2006.01) |
| ***A61K 8/34*** | (2006.01) |
| ***A61K 8/41*** | (2006.01) |
| ***A61K 8/89*** | (2006.01) |
| ***A61Q 5/00*** | (2006.01) |

(52) U.S. Cl.

CPC .............. *A61K 8/342* (2013.01); *A61K 8/361* (2013.01); *A61K 8/416* (2013.01); *A61K 8/89* (2013.01); *A61Q 5/00* (2013.01); *A61K 2800/87* (2013.01); *A61K 2800/882* (2013.01)

(58) Field of Classification Search

None

See application file for complete search history.

(56) References Cited

U.S. PATENT DOCUMENTS

| | | | |
|---|---|---|---|
| 1,108,367 | A | 8/1914 | Holtermann |
| 1,489,388 | A | 4/1924 | Glenn |
| 1,600,340 | A | 9/1926 | Hoffman |
| 1,612,255 | A | 12/1926 | William |
| 2,438,091 | A | 3/1948 | Lynch |
| 2,528,378 | A | 10/1950 | Mannheimer |
| 2,658,072 | A | 11/1953 | Milton |
| 2,809,971 | A | 10/1957 | Jack et al. |
| 2,879,231 | A | 3/1959 | Marshall |
| 3,219,656 | A | 11/1965 | Boettner |
| 3,236,733 | A | 2/1966 | Karsten et al. |
| 3,373,208 | A | 3/1968 | Blumenthal |
| 3,636,113 | A | 1/1972 | Hall |
| 3,709,437 | A | 1/1973 | Wright |
| 3,716,498 | A | 2/1973 | Hall |
| 3,753,196 | A | 8/1973 | Kurtz et al. |
| 3,761,418 | A | 9/1973 | Parran |
| 3,792,068 | A | 2/1974 | Luedders et al. |
| 3,887,692 | A | 6/1975 | Gilman |
| 3,904,741 | A | 9/1975 | Jones et al. |
| 3,950,532 | A | 4/1976 | Bouillon et al. |
| 3,958,581 | A | 5/1976 | Abegg et al. |
| 3,959,160 | A | 5/1976 | Horsler et al. |
| 3,962,418 | A | 6/1976 | Birkofer |
| 4,049,792 | A | 9/1977 | Elsnau |
| 4,089,945 | A | 5/1978 | Brinkman et al. |
| 4,120,948 | A | 10/1978 | Shelton |
| 4,137,180 | A | 1/1979 | Naik |
| 4,237,155 | A | 12/1980 | Kardouche |
| 4,275,055 | A | 6/1981 | Nachtigal |
| 4,309,119 | A | 1/1982 | Wittersheim |
| 4,323,683 | A | 4/1982 | Bolich, Jr. et al. |
| 4,329,334 | A | 5/1982 | Su et al. |
| 4,345,080 | A | 8/1982 | Bolich, Jr. |
| 4,359,456 | A | 11/1982 | Gosling et al. |
| 4,379,753 | A | 4/1983 | Bolich, Jr. |
| 4,430,243 | A | 2/1984 | Bragg |

(Continued)

FOREIGN PATENT DOCUMENTS

| | | | |
|---|---|---|---|
| BR | 199400875 | A | 10/1995 |
| CA | 704195 | A | 2/1965 |

(Continued)

OTHER PUBLICATIONS

Anonymous: "Acne Foaming Cleanser", Database GNPD [Online] MINTEL, XP055591421, Jul. 29, 2016, 03 Pages.
Anonymous: "Naturally Rich Moisturizing Shampoo", Database GNPD [Online] Mintel, XP55897729, Mar. 27, 2019, 03 Pages.
Anonymous: "Shampoo C", Database GNPD [Online] MINTEL, Sep. 29, 2011, 03 Pages.
"Anti-Dandruff Shampoo", Mintel Database, Record No. 752198, dated Aug. 2007 ; pp. 1-3.
"Cleansing Pack" Mintel Database, www.gnpd.com, Apr. 6, 2018, 2 pages.
"Comparative Study on the Chemical constituents of Aloe Vera and Aloe Kula in China", Zhang Xiaohua et al., Flavor Cosmetics, No. 63, dated Dec 31, 2000, pp. 7-11.
"Conditioner Soap Bar" Mintel Database, www.gnpd.com, Feb. 15, 2018, 4 pages.
"Dandruff Control Shampoo", Mintel Database, Record No. 2300131, dated Jan. 2014; pp. 1-2.

(Continued)

*Primary Examiner* — Susan T Tran
(74) *Attorney, Agent, or Firm* — Abbey A. Lopez; John G. Powell

(57) ABSTRACT

A hair conditioning particle that includes a surfactant, a high melting point fatty compound and a benefit agent. The particle is solid and generally contains less than 50% water or other liquids. When added to water or an aqueous personal care composition, the particles may provide at least one of the following benefits: boosting rheology, especially storage modulus (G'); boosting conditioning benefits; an aesthetic benefit such as a color change, an anti-dandruff benefit, a sensate such as heating or cooling; and/or a scent. The particles and compositions containing the particles exhibit good stability.

17 Claims, No Drawings

(56) References Cited

U.S. PATENT DOCUMENTS

| | | | |
|---|---|---|---|
| 4,470,982 | A | 9/1984 | Winkler |
| 4,726,945 | A | 2/1988 | Patel |
| 4,732,696 | A | 3/1988 | Urfer |
| 4,795,327 | A | 1/1989 | Gaylord |
| 4,830,774 | A | 5/1989 | Lapetina et al. |
| 4,839,166 | A | 6/1989 | Grollier et al. |
| 4,854,333 | A | 8/1989 | Inman et al. |
| 4,867,971 | A | 9/1989 | Ryan et al. |
| 4,891,214 | A | 1/1990 | Stevens |
| 4,925,585 | A | 5/1990 | Strauss et al. |
| 4,931,274 | A | 6/1990 | Barabino et al. |
| 4,973,416 | A | 11/1990 | Kennedy |
| 4,985,238 | A | 1/1991 | Tanner et al. |
| 4,997,641 | A | 3/1991 | Hartnett |
| 5,019,375 | A | 5/1991 | Tanner et al. |
| 5,093,112 | A | 3/1992 | Birtwistle et al. |
| 5,104,646 | A | 4/1992 | Bolich, Jr. |
| 5,106,609 | A | 4/1992 | Bolich, Jr. |
| 5,135,747 | A | 8/1992 | Faryniarz et al. |
| 5,156,834 | A | 10/1992 | Beckmeyer et al. |
| 5,294,644 | A | 3/1994 | Login et al. |
| 5,296,157 | A | 3/1994 | Macgilp et al. |
| 5,296,622 | A | 3/1994 | Uphues |
| 5,298,640 | A | 3/1994 | Callaghan et al. |
| 5,332,569 | A | 7/1994 | Wood et al. |
| 5,364,031 | A | 11/1994 | Taniguchi et al. |
| 5,374,421 | A | 12/1994 | Tashiro |
| 5,374,614 | A | 12/1994 | Behan et al. |
| 5,409,695 | A | 4/1995 | Abrutyn et al. |
| 5,415,810 | A | 5/1995 | Lee et al. |
| 5,417,965 | A | 5/1995 | Janchitraponvej et al. |
| 5,429,816 | A | 7/1995 | Hofrichter et al. |
| 5,439,682 | A | 8/1995 | Wivell |
| 5,441,659 | A | 8/1995 | Minor |
| 5,486,303 | A | 1/1996 | Capeci |
| 5,489,392 | A | 2/1996 | Capeci |
| 5,496,488 | A | 3/1996 | Kacher et al. |
| 5,516,448 | A | 5/1996 | Capeci |
| 5,536,493 | A | 7/1996 | Dubief |
| 5,554,588 | A | 9/1996 | Behan et al. |
| 5,560,918 | A | 10/1996 | Wivell |
| 5,565,422 | A | 10/1996 | Del |
| 5,569,645 | A | 10/1996 | Dinniwell |
| 5,574,005 | A | 11/1996 | Welch |
| 5,576,282 | A | 11/1996 | Miracle |
| 5,578,298 | A | 11/1996 | Berthiaume |
| 5,595,967 | A | 1/1997 | Miracle |
| 5,597,936 | A | 1/1997 | Perkins |
| 5,599,549 | A | 2/1997 | Wivell |
| 5,624,666 | A | 4/1997 | Coffindaffer et al. |
| 5,635,469 | A | 6/1997 | Fowler et al. |
| 5,665,267 | A | 9/1997 | Dowell et al. |
| 5,691,297 | A | 11/1997 | Nassano |
| 5,714,137 | A | 2/1998 | Trinh |
| 5,747,436 | A | 5/1998 | Patel |
| 5,776,444 | A | 7/1998 | Birtwistle et al. |
| 5,800,897 | A | 9/1998 | Sharma |
| 5,816,446 | A | 10/1998 | Steindorf et al. |
| 5,830,440 | A | 11/1998 | Sturla et al. |
| 5,853,618 | A | 12/1998 | Barker |
| 5,876,705 | A | 3/1999 | Uchiyama |
| 5,879,584 | A | 3/1999 | Bianchetti |
| 5,891,424 | A | 4/1999 | Bretzler et al. |
| 5,902,225 | A | 5/1999 | Monson |
| 5,904,932 | A | 5/1999 | De |
| 5,925,603 | A | 7/1999 | D |
| 5,942,217 | A | 8/1999 | Woo et al. |
| 5,955,066 | A | 9/1999 | Sako |
| 5,976,514 | A | 11/1999 | Guskey et al. |
| 5,980,877 | A | 11/1999 | Baravetto |
| 5,985,255 | A | 11/1999 | Vanlerberghe et al. |
| 5,985,939 | A | 11/1999 | Minor |
| 6,015,547 | A | 1/2000 | Yam |
| 6,015,780 | A | 1/2000 | Llosas Bigorra et al. |
| 6,020,303 | A | 2/2000 | Cripe et al. |
| 6,039,933 | A | 3/2000 | Samain et al. |
| 6,046,152 | A | 4/2000 | Vinson et al. |
| 6,060,443 | A | 5/2000 | Cripe et al. |
| 6,087,309 | A | 7/2000 | Vinson et al. |
| 6,110,451 | A | 8/2000 | Matz et al. |
| 6,133,222 | A | 10/2000 | Vinson et al. |
| 6,139,828 | A | 10/2000 | Mccullough |
| 6,153,567 | A | 11/2000 | Hughes |
| 6,153,569 | A | 11/2000 | Halloran |
| 6,162,834 | A | 12/2000 | Sebillotte-Arnaud et al. |
| 6,180,121 | B1 | 1/2001 | Guenin et al. |
| 6,225,464 | B1 | 5/2001 | Hiler, II |
| 6,231,844 | B1 | 5/2001 | Nambu |
| 6,232,302 | B1 | 5/2001 | Alberico et al. |
| 6,248,135 | B1 | 6/2001 | Trinh et al. |
| 6,268,431 | B1 | 7/2001 | Snyder et al. |
| 6,284,225 | B1 | 9/2001 | Bhatt |
| 6,297,203 | B1 | 10/2001 | Guskey |
| 6,329,331 | B1 | 12/2001 | Aronson |
| 6,335,312 | B1 | 1/2002 | Coffindaffer et al. |
| 6,352,688 | B1 | 3/2002 | Scavone et al. |
| 6,386,392 | B1 | 5/2002 | Argentieri |
| 6,413,920 | B1 | 7/2002 | Bettiol |
| 6,423,305 | B1 | 7/2002 | Cauwet-Martin et al. |
| 6,426,326 | B1 | 7/2002 | Mitra et al. |
| 6,436,442 | B1 | 8/2002 | Woo et al. |
| 6,451,300 | B1 | 9/2002 | Dunlop et al. |
| 6,488,943 | B1 | 12/2002 | Beerse et al. |
| 6,511,669 | B1 | 1/2003 | Garnier et al. |
| 6,565,863 | B1 | 5/2003 | Guillou et al. |
| 6,579,907 | B1 | 6/2003 | Sebillotte-Arnaud et al. |
| 6,627,585 | B1 | 9/2003 | Steer |
| 6,642,194 | B2 | 11/2003 | Harrison |
| 6,649,155 | B1 | 11/2003 | Dunlop et al. |
| 6,656,923 | B1 | 12/2003 | Trinh |
| 6,660,288 | B1 | 12/2003 | Behan et al. |
| 6,679,324 | B2 | 1/2004 | Den et al. |
| 6,716,455 | B2 | 4/2004 | Birkel |
| 6,716,805 | B1 | 4/2004 | Sherry |
| 6,719,967 | B1 | 4/2004 | Brown |
| 6,740,713 | B1 | 5/2004 | Busch et al. |
| 6,743,760 | B1 | 6/2004 | Hardy et al. |
| 6,764,986 | B1 | 7/2004 | Busch et al. |
| 6,767,507 | B1 | 7/2004 | Woo et al. |
| 6,794,356 | B2 | 9/2004 | Turner |
| 6,814,088 | B2 | 11/2004 | Barnabas et al. |
| 6,827,795 | B1 | 12/2004 | Kasturi et al. |
| 6,831,046 | B2 | 12/2004 | Carew et al. |
| 6,869,923 | B1 | 3/2005 | Cunningham |
| 6,878,368 | B2 | 4/2005 | Ohta |
| 6,897,253 | B2 | 5/2005 | Schmucker-castner |
| 6,908,889 | B2 | 6/2005 | Niemiec et al. |
| 6,930,078 | B2 | 8/2005 | Wells |
| 6,992,054 | B2 | 1/2006 | Unilever |
| 7,018,978 | B2 | 3/2006 | Miracle et al. |
| 7,030,068 | B2 | 4/2006 | Clare et al. |
| 7,100,767 | B2 | 9/2006 | Chomik et al. |
| 7,151,079 | B2 | 12/2006 | Fack et al. |
| 7,172,099 | B2 | 2/2007 | Hoefte |
| 7,202,198 | B2 | 4/2007 | Gordon et al. |
| 7,217,752 | B2 | 5/2007 | Schmucker-Castner et al. |
| 7,220,408 | B2 | 5/2007 | Decoster et al. |
| 7,223,361 | B2 | 5/2007 | Kvietok |
| 7,223,385 | B2 | 5/2007 | Gawtrey et al. |
| 7,303,744 | B2 | 12/2007 | Wells |
| 7,462,585 | B2 | 12/2008 | Uehara |
| 7,485,289 | B2 | 2/2009 | Gawtrey et al. |
| 7,504,094 | B2 | 3/2009 | Decoster et al. |
| 7,531,497 | B2 | 5/2009 | Midha et al. |
| 7,541,320 | B2 | 6/2009 | Dabkowski et al. |
| 7,598,213 | B2 | 10/2009 | Geary et al. |
| 7,659,233 | B2 | 2/2010 | Conopco |
| 7,666,825 | B2 | 2/2010 | Wagner et al. |
| 7,674,759 | B2 | 3/2010 | Tsaur |
| 7,730,552 | B2 | 6/2010 | Ota et al. |
| 7,759,378 | B2 | 7/2010 | Philippe |
| 7,776,347 | B2 | 8/2010 | Kerschner et al. |
| 7,820,609 | B2 | 10/2010 | Soffin et al. |
| 7,829,514 | B2 | 11/2010 | Paul et al. |

(56) References Cited

U.S. PATENT DOCUMENTS

| | | | |
|---|---|---|---|
| 7,841,036 B2 | 11/2010 | Smith |
| 7,867,505 B2 | 1/2011 | Elliott et al. |
| 7,928,053 B2 | 4/2011 | Hecht et al. |
| 7,977,288 B2 | 7/2011 | SenGupta |
| 8,007,545 B2 | 8/2011 | Fujii et al. |
| 8,017,108 B2 | 9/2011 | Baker |
| 8,058,500 B2 | 11/2011 | Sojka et al. |
| 8,084,407 B2 | 12/2011 | Soffin et al. |
| 8,088,721 B2 | 1/2012 | Soffin et al. |
| 8,119,168 B2 | 2/2012 | Johnson |
| 8,124,063 B2 | 2/2012 | Harichian et al. |
| 8,158,571 B2 | 4/2012 | Alonso |
| 8,300,949 B2 | 10/2012 | Xu |
| 8,322,631 B2 | 12/2012 | Richardson et al. |
| 8,343,469 B2 | 1/2013 | Bierganns et al. |
| 8,349,300 B2 | 1/2013 | Wells |
| 8,349,301 B2 | 1/2013 | Wells |
| 8,349,302 B2 | 1/2013 | Johnson |
| 8,357,359 B2 | 1/2013 | Woo et al. |
| 8,361,448 B2 | 1/2013 | Johnson |
| 8,361,449 B2 | 1/2013 | Wells |
| 8,361,450 B2 | 1/2013 | Johnson |
| 8,367,048 B2 | 2/2013 | Wells |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,470,305 B2 | 6/2013 | Johnson |
| 8,491,877 B2 | 7/2013 | Schwartz et al. |
| 8,524,280 B2 | 9/2013 | Fatmi et al. |
| 8,539,631 B2 | 9/2013 | Catalfamo et al. |
| 8,574,561 B1 | 11/2013 | Patel et al. |
| 8,580,725 B2 | 11/2013 | Kuhlman et al. |
| 8,609,600 B2 | 12/2013 | Warr |
| 8,628,760 B2 | 1/2014 | Carter et al. |
| 8,629,095 B2 | 1/2014 | Deleersnyder |
| 8,653,014 B2 | 2/2014 | Hilvert |
| 8,675,919 B2 | 3/2014 | Maladen |
| 8,679,316 B2 | 3/2014 | Brunner et al. |
| 8,680,035 B2 | 3/2014 | Kuhlman et al. |
| 8,699,751 B2 | 4/2014 | Maladen |
| 8,709,337 B2 | 4/2014 | Gruenbacher et al. |
| 8,709,385 B2 | 4/2014 | Tamarkin |
| 8,741,275 B2 | 6/2014 | Dente et al. |
| 8,741,363 B2 | 6/2014 | Albrecht et al. |
| 8,771,765 B1 | 7/2014 | Fernandez |
| 8,772,354 B2 | 7/2014 | Williams et al. |
| 8,795,635 B2 | 8/2014 | Tamarkin et al. |
| 8,877,316 B2 | 11/2014 | Hasenoehrl et al. |
| 8,883,698 B2 | 11/2014 | Scheibel et al. |
| 8,931,711 B2 | 1/2015 | Gruenbacher |
| 8,980,239 B2 | 3/2015 | Staudigel et al. |
| 8,987,187 B2 | 3/2015 | Smets et al. |
| 9,006,162 B1 | 4/2015 | Rizk |
| 9,186,642 B2 | 11/2015 | Dihora et al. |
| 9,187,407 B2 | 11/2015 | Koshti et al. |
| 9,265,727 B1 | 2/2016 | Lowenborg |
| 9,271,908 B2 | 3/2016 | Allef |
| 9,272,164 B2 | 3/2016 | Johnson et al. |
| 9,296,550 B2 | 3/2016 | Smith |
| 9,308,398 B2 | 4/2016 | Hutton et al. |
| 9,393,447 B2 | 7/2016 | Zasloff |
| 9,428,616 B2 | 8/2016 | Wagner |
| 9,511,007 B2 | 12/2016 | Frantz et al. |
| 9,512,275 B2 | 12/2016 | Wagner |
| 9,539,444 B2 | 1/2017 | Kinoshita |
| 9,610,239 B2 | 4/2017 | Feng |
| 9,655,821 B2 | 5/2017 | Carter et al. |
| 9,662,291 B2 | 5/2017 | Johnson et al. |
| 9,682,021 B2 | 6/2017 | Tamarkin et al. |
| 9,724,283 B2 | 8/2017 | Rizk |
| 9,776,787 B2 | 10/2017 | Nakajima |
| 9,827,202 B2 | 11/2017 | Mcginity et al. |
| 9,949,901 B2 | 4/2018 | Zhao et al. |
| 9,949,911 B2 | 4/2018 | Cetti |
| 9,968,535 B2 | 5/2018 | Kitko et al. |
| 9,968,537 B2 | 5/2018 | Sharma |
| 9,993,419 B2 | 6/2018 | Glenn, Jr. |
| 9,993,420 B2 | 6/2018 | Glenn, Jr. et al. |
| 10,039,706 B2 | 8/2018 | Meralli et al. |
| 10,039,939 B2 | 8/2018 | Xavier et al. |
| 10,092,492 B2 | 10/2018 | Terrisse |
| 10,113,140 B2 | 10/2018 | Frankenbach |
| 10,182,976 B2 | 1/2019 | Staudigel |
| 10,238,685 B2 | 3/2019 | Dunn et al. |
| 10,265,261 B2 | 4/2019 | Park et al. |
| 10,311,575 B2 | 6/2019 | Stofel |
| 10,392,625 B2 | 8/2019 | Jin et al. |
| 10,426,713 B2 | 10/2019 | Song et al. |
| 10,441,519 B2 | 10/2019 | Zhao |
| 10,500,150 B2 | 12/2019 | Matsuo |
| 10,552,557 B2 | 2/2020 | Frankenbach et al. |
| 10,610,473 B2 | 4/2020 | Hertenstein et al. |
| 10,653,590 B2 | 5/2020 | Torres Rivera |
| 10,751,272 B2 | 8/2020 | Yokogi |
| 10,799,434 B2 | 10/2020 | Torres Rivera |
| 10,842,720 B2 | 11/2020 | Thompson |
| 10,881,597 B2 | 1/2021 | Lane et al. |
| 10,888,505 B2 | 1/2021 | Johnson |
| 10,912,730 B2 | 2/2021 | Fevola |
| 10,912,732 B2 | 2/2021 | Gillis |
| 11,058,620 B2 | 7/2021 | Yokogi |
| 11,116,703 B2 | 9/2021 | Song et al. |
| 11,116,704 B2 | 9/2021 | Song et al. |
| 11,129,775 B2 | 9/2021 | Song et al. |
| 11,129,786 B2 | 9/2021 | Adamy |
| 11,186,636 B2 | 11/2021 | Foltz |
| 11,197,809 B2 | 12/2021 | Hertenstein et al. |
| 11,197,810 B2 | 12/2021 | Hertenstein et al. |
| 11,334,694 B2 | 5/2022 | Cetti et al. |
| 11,334,695 B2 | 5/2022 | Cetti et al. |
| 11,478,412 B2 | 10/2022 | Kadir |
| 11,679,065 B2 | 6/2023 | Johnson et al. |
| 11,865,198 B2 | 1/2024 | Kroger Lyons |
| 11,904,036 B2 | 2/2024 | Song |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0012646 A1 | 1/2002 | Royce et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0003070 A1 | 1/2003 | Eggers et al. |
| 2003/0008787 A1 | 1/2003 | Mcgee et al. |
| 2003/0008790 A1 | 1/2003 | Carew |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0050217 A1 | 3/2003 | Instone et al. |
| 2003/0059377 A1 | 3/2003 | Riley |
| 2003/0083210 A1 | 5/2003 | Goldberg |
| 2003/0103923 A1 | 6/2003 | Ohta |
| 2003/0108501 A1 | 6/2003 | Hofrichter |
| 2003/0113354 A1 | 6/2003 | Schmid |
| 2003/0134759 A1 | 7/2003 | Geary et al. |
| 2003/0147842 A1 | 8/2003 | Restle et al. |
| 2003/0154561 A1 | 8/2003 | Patel |
| 2003/0161802 A1 | 8/2003 | Flammer |
| 2003/0180238 A1 | 9/2003 | Sakurai et al. |
| 2003/0180246 A1 | 9/2003 | Frantz et al. |
| 2003/0185867 A1 | 10/2003 | Kerschner et al. |
| 2003/0192922 A1 | 10/2003 | Ceppaluni et al. |
| 2003/0199403 A1 | 10/2003 | Wells |
| 2003/0202952 A1 | 10/2003 | Wells et al. |
| 2003/0223951 A1 | 12/2003 | Geary et al. |
| 2003/0223952 A1 | 12/2003 | Wells |
| 2003/0228272 A1 | 12/2003 | Amjad et al. |
| 2004/0005285 A1 | 1/2004 | Midha |
| 2004/0014879 A1 | 1/2004 | Denzer et al. |
| 2004/0064117 A1 | 4/2004 | Hammons |
| 2004/0131660 A1 | 7/2004 | Lange et al. |

(56) References Cited

U.S. PATENT DOCUMENTS

| | | | |
|---|---|---|---|
| 2004/0144863 | A1 | 7/2004 | Kendrick |
| 2004/0151793 | A1 | 8/2004 | Paspaleeva-kuhn et al. |
| 2004/0157754 | A1 | 8/2004 | Geary et al. |
| 2004/0229963 | A1 | 11/2004 | Stephane |
| 2004/0234484 | A1 | 11/2004 | Peffly |
| 2004/0235689 | A1 | 11/2004 | Sakai et al. |
| 2005/0003975 | A1 | 1/2005 | Browne et al. |
| 2005/0003980 | A1 | 1/2005 | Baker |
| 2005/0020468 | A1 | 1/2005 | Frantz et al. |
| 2005/0136011 | A1 | 6/2005 | Nekludoff |
| 2005/0152863 | A1 | 7/2005 | Brautigam |
| 2005/0192207 | A1 | 9/2005 | Morgan et al. |
| 2005/0201967 | A1 | 9/2005 | Albrecht et al. |
| 2005/0202984 | A1 | 9/2005 | Schwartz et al. |
| 2005/0208106 | A1 | 9/2005 | Lange et al. |
| 2005/0227902 | A1 | 10/2005 | Erazo-majewicz et al. |
| 2005/0233929 | A1 | 10/2005 | Queen |
| 2005/0245407 | A1 | 11/2005 | Ishihara |
| 2005/0276831 | A1 | 12/2005 | Dihora |
| 2006/0002880 | A1 | 1/2006 | Peffly |
| 2006/0005333 | A1 | 1/2006 | Catalfamo et al. |
| 2006/0009337 | A1 | 1/2006 | Smith |
| 2006/0030509 | A1 | 2/2006 | Modi |
| 2006/0034778 | A1 | 2/2006 | Kitano et al. |
| 2006/0057075 | A1 | 3/2006 | Arkin et al. |
| 2006/0057097 | A1 | 3/2006 | Derici |
| 2006/0079417 | A1 | 4/2006 | Wagner |
| 2006/0079418 | A1 | 4/2006 | Wagner et al. |
| 2006/0079419 | A1 | 4/2006 | Wagner et al. |
| 2006/0079420 | A1 | 4/2006 | Wagner et al. |
| 2006/0079421 | A1 | 4/2006 | Wagner et al. |
| 2006/0084589 | A1 | 4/2006 | Vlad et al. |
| 2006/0090777 | A1 | 5/2006 | Hecht et al. |
| 2006/0094610 | A1 | 5/2006 | Yamato et al. |
| 2006/0110415 | A1 | 5/2006 | Gupta |
| 2006/0120982 | A1 | 6/2006 | Derici et al. |
| 2006/0120988 | A1 | 6/2006 | Bailey et al. |
| 2006/0127338 | A1 | 6/2006 | Morita et al. |
| 2006/0135397 | A1 | 6/2006 | Bissey-beugras |
| 2006/0166857 | A1 | 7/2006 | Surburg et al. |
| 2006/0171911 | A1 | 8/2006 | Schwartz et al. |
| 2006/0182703 | A1 | 8/2006 | Arisz |
| 2006/0183662 | A1 | 8/2006 | Crotty |
| 2006/0210139 | A1 | 9/2006 | Carroll |
| 2006/0229227 | A1 | 10/2006 | Goldman |
| 2006/0248663 | A1 | 11/2006 | Tremblay et al. |
| 2006/0252662 | A1 | 11/2006 | Soffin |
| 2006/0263319 | A1 | 11/2006 | Fan et al. |
| 2006/0269503 | A1 | 11/2006 | Yamazaki |
| 2006/0276357 | A1 | 12/2006 | Smith, III et al. |
| 2006/0292104 | A1 | 12/2006 | Guskey |
| 2007/0003499 | A1 | 1/2007 | Shen et al. |
| 2007/0020263 | A1 | 1/2007 | Shitara et al. |
| 2007/0072781 | A1 | 3/2007 | Soffin et al. |
| 2007/0110700 | A1 | 5/2007 | Wells |
| 2007/0117737 | A1 | 5/2007 | Artiga et al. |
| 2007/0154402 | A1 | 7/2007 | Trumbore et al. |
| 2007/0155637 | A1 | 7/2007 | Smith, III et al. |
| 2007/0160555 | A1 | 7/2007 | Staudigel |
| 2007/0179207 | A1 | 8/2007 | Fernandez de Castro et al. |
| 2007/0224152 | A1 | 9/2007 | Sakai |
| 2007/0225193 | A1 | 9/2007 | Kuhlman et al. |
| 2007/0269397 | A1 | 11/2007 | Terada |
| 2007/0275866 | A1 | 11/2007 | Dykstra |
| 2007/0292380 | A1 | 12/2007 | Staudigel |
| 2007/0298994 | A1 | 12/2007 | Finke et al. |
| 2008/0003245 | A1 | 1/2008 | Kroepke et al. |
| 2008/0008668 | A1 | 1/2008 | Harichian et al. |
| 2008/0019928 | A1 | 1/2008 | Franzke |
| 2008/0063618 | A1 | 3/2008 | Johnson |
| 2008/0138442 | A1 | 6/2008 | Johnson |
| 2008/0152610 | A1 | 6/2008 | Cajan |
| 2008/0160093 | A1 | 7/2008 | Schwartz et al. |
| 2008/0176780 | A1 | 7/2008 | Warr |
| 2008/0187507 | A1 | 8/2008 | Johnson |
| 2008/0194454 | A1 | 8/2008 | Morgan |
| 2008/0206179 | A1 | 8/2008 | Peffly et al. |
| 2008/0229512 | A1 | 9/2008 | Syed et al. |
| 2008/0260655 | A1 | 10/2008 | Tamarkin et al. |
| 2008/0260665 | A1 | 10/2008 | Guerchet et al. |
| 2008/0261844 | A1 | 10/2008 | Ruppert et al. |
| 2008/0299054 | A1 | 12/2008 | Chandar et al. |
| 2008/0317698 | A1 | 12/2008 | Wells et al. |
| 2009/0005280 | A1 | 1/2009 | Woo et al. |
| 2009/0029900 | A1 | 1/2009 | Cetti et al. |
| 2009/0041702 | A1 | 2/2009 | Molenda |
| 2009/0062406 | A1 | 3/2009 | Loeffler |
| 2009/0155383 | A1 | 6/2009 | Kitko et al. |
| 2009/0178210 | A1 | 7/2009 | Bistram |
| 2009/0197784 | A1 | 8/2009 | Ainger |
| 2009/0221463 | A1 | 9/2009 | Kitko et al. |
| 2009/0240223 | A1 | 9/2009 | Warren |
| 2009/0246236 | A1 | 10/2009 | Kitko |
| 2009/0312223 | A1 | 12/2009 | Yang et al. |
| 2009/0312224 | A1 | 12/2009 | Yang et al. |
| 2009/0324505 | A1 | 12/2009 | Seidling |
| 2009/0324532 | A1 | 12/2009 | Okada et al. |
| 2010/0000116 | A1 | 1/2010 | Aouad et al. |
| 2010/0001116 | A1 | 1/2010 | Johnson |
| 2010/0009285 | A1 | 1/2010 | Daems et al. |
| 2010/0061946 | A1 | 3/2010 | Scherner et al. |
| 2010/0087357 | A1 | 4/2010 | Morgan, III et al. |
| 2010/0143280 | A1 | 6/2010 | Yokogi |
| 2010/0152083 | A1 | 6/2010 | Velazquez |
| 2010/0168251 | A1 | 7/2010 | Warr et al. |
| 2010/0183539 | A1 | 7/2010 | Bernhardt |
| 2010/0215775 | A1 | 8/2010 | Schmaus et al. |
| 2010/0287710 | A1 | 11/2010 | Denutte et al. |
| 2010/0310644 | A1 | 12/2010 | Liebmann |
| 2010/0322878 | A1 | 12/2010 | Stella et al. |
| 2011/0008267 | A1 | 1/2011 | Arkin et al. |
| 2011/0023266 | A1 | 2/2011 | Gross et al. |
| 2011/0098209 | A1 | 4/2011 | Smets et al. |
| 2011/0107524 | A1 | 5/2011 | Chieffi et al. |
| 2011/0118691 | A1 | 5/2011 | Nishitani |
| 2011/0139170 | A1 | 6/2011 | Hippe et al. |
| 2011/0150815 | A1 | 6/2011 | Woo et al. |
| 2011/0165107 | A1 | 7/2011 | Derks et al. |
| 2011/0171155 | A1 | 7/2011 | Federle |
| 2011/0177017 | A1 | 7/2011 | Coffindaffer et al. |
| 2011/0232668 | A1 | 9/2011 | Hoffmann et al. |
| 2011/0245126 | A1 | 10/2011 | Tsaur et al. |
| 2011/0245134 | A1 | 10/2011 | Smets |
| 2011/0245136 | A1 | 10/2011 | Smets |
| 2011/0268778 | A1 | 11/2011 | Dihora et al. |
| 2011/0268802 | A1 | 11/2011 | Dihora |
| 2011/0269657 | A1 | 11/2011 | Dihora |
| 2011/0300095 | A1 | 12/2011 | Dente et al. |
| 2011/0303766 | A1 | 12/2011 | Smith |
| 2011/0305739 | A1 | 12/2011 | Royce |
| 2011/0305778 | A1 | 12/2011 | Caggioni et al. |
| 2011/0308555 | A1 | 12/2011 | Smets et al. |
| 2011/0308556 | A1 | 12/2011 | Smets et al. |
| 2011/0319790 | A1 | 12/2011 | Kost et al. |
| 2012/0004328 | A1 | 1/2012 | Huchel et al. |
| 2012/0009285 | A1 | 1/2012 | Wei et al. |
| 2012/0014901 | A1 | 1/2012 | Sunkel et al. |
| 2012/0031419 | A1 | 2/2012 | Batt |
| 2012/0034173 | A1 | 2/2012 | Batt |
| 2012/0052031 | A1 | 3/2012 | Troccaz et al. |
| 2012/0100091 | A1 | 4/2012 | Hata et al. |
| 2012/0100092 | A1 | 4/2012 | Murray |
| 2012/0129924 | A1 | 5/2012 | Park et al. |
| 2012/0164198 | A1 | 6/2012 | Johnson et al. |
| 2012/0219610 | A1 | 8/2012 | Smith, III et al. |
| 2012/0230936 | A1 | 9/2012 | Mikkelsen |
| 2012/0237469 | A1 | 9/2012 | Dente et al. |
| 2012/0246851 | A1 | 10/2012 | Smith, III et al. |
| 2012/0258150 | A1 | 10/2012 | Rauckhorst et al. |
| 2012/0291911 | A1 | 11/2012 | Smith |
| 2012/0309660 | A1 | 12/2012 | Kawasoe |
| 2012/0316095 | A1 | 12/2012 | Wei et al. |
| 2013/0022556 | A1 | 1/2013 | Gonzales et al. |
| 2013/0029932 | A1 | 1/2013 | Kachi et al. |

(56) References Cited

U.S. PATENT DOCUMENTS

2013/0034515 A1 2/2013 Stone et al.
2013/0043145 A1 2/2013 Smith, III et al.
2013/0043146 A1 2/2013 Smith, III et al.
2013/0043147 A1 2/2013 Smith, III et al.
2013/0045285 A1 2/2013 Stella et al.
2013/0053295 A1 2/2013 Kinoshita et al.
2013/0053300 A1 2/2013 Scheibel et al.
2013/0071346 A1 3/2013 Okada
2013/0089586 A1 4/2013 Johnson et al.
2013/0089587 A1 4/2013 Staudigel
2013/0115173 A1 5/2013 Trumbore et al.
2013/0136713 A1 5/2013 Terada et al.
2013/0143784 A1 6/2013 Rizk
2013/0150338 A1 6/2013 Ananthapadmanabhan
2013/0156712 A1 6/2013 Frantz
2013/0189212 A1 7/2013 Jawale et al.
2013/0211952 A1 8/2013 Sugaya
2013/0216491 A1 8/2013 Ogihara et al.
2013/0243718 A1 9/2013 Pasquet
2013/0244922 A1 9/2013 Bartelt
2013/0266642 A1 10/2013 Hollingshead et al.
2013/0280192 A1 10/2013 Carter et al.
2013/0280202 A1 10/2013 Stella et al.
2013/0284195 A1 10/2013 Murdock
2013/0287720 A1 10/2013 Tetsu et al.
2013/0296289 A1 11/2013 Hall et al.
2013/0319463 A1 12/2013 Policicchio
2014/0037703 A1 2/2014 Dihora et al.
2014/0039066 A1 2/2014 Grimadell et al.
2014/0086893 A1 3/2014 Gutmann et al.
2014/0112879 A1 4/2014 Molenda et al.
2014/0112964 A1 4/2014 Wu
2014/0127149 A1 5/2014 Lepilleur
2014/0131395 A1 5/2014 Chang
2014/0134125 A1 5/2014 Dahl
2014/0162979 A1 6/2014 Palla-venkata
2014/0171471 A1 6/2014 Krueger
2014/0186864 A1 7/2014 Kato et al.
2014/0201927 A1 7/2014 Bianchetti et al.
2014/0216495 A1 8/2014 Bureiko
2014/0221269 A1 8/2014 Sobel et al.
2014/0228268 A1 8/2014 Fahl et al.
2014/0237732 A1 8/2014 Zuedel Fernandes et al.
2014/0246515 A1 9/2014 Nakajima
2014/0308227 A1 10/2014 Mabille
2014/0309154 A1 10/2014 Carter et al.
2014/0335041 A1 11/2014 Peffly et al.
2014/0348884 A1 11/2014 Hilvert et al.
2014/0348886 A1 11/2014 Johnson et al.
2014/0349902 A1 11/2014 Allef et al.
2015/0017152 A1 1/2015 Potechin et al.
2015/0021496 A1 1/2015 Shabbir
2015/0037273 A1 2/2015 Wagner
2015/0050231 A1 2/2015 Murase
2015/0071977 A1 3/2015 Dihora
2015/0093420 A1 4/2015 Snyder
2015/0093429 A1 4/2015 Carter et al.
2015/0098921 A1 4/2015 Franzke et al.
2015/0099684 A1 4/2015 Boutique
2015/0108163 A1 4/2015 Smith et al.
2015/0110728 A1 4/2015 Jayaswal
2015/0141310 A1 5/2015 Smets et al.
2015/0147286 A1 5/2015 Barrera
2015/0157548 A1 6/2015 De Feij et al.
2015/0216770 A1 8/2015 Takahashi et al.
2015/0218496 A1 8/2015 Schmiedel et al.
2015/0231045 A1 8/2015 Krohn et al.
2015/0262354 A1 9/2015 Periaswamy
2015/0297489 A1 10/2015 Kleinen et al.
2015/0299400 A1 10/2015 Wagner et al.
2015/0313818 A1 11/2015 Stagg
2015/0352027 A1 12/2015 Thomas et al.
2015/0359725 A1 12/2015 Glenn, Jr. et al.
2015/0359726 A1 12/2015 Glenn, Jr. et al.
2015/0359728 A1 12/2015 Glenn, Jr. et al.
2016/0008257 A1 1/2016 Zhou et al.
2016/0022566 A1 1/2016 Figura
2016/0089317 A1 3/2016 Cetti et al.
2016/0089322 A1 3/2016 Santos Nogueira et al.
2016/0089462 A1 3/2016 Frankenbach
2016/0089464 A1 3/2016 Frankenbach et al.
2016/0089465 A1 3/2016 Frankenbach et al.
2016/0090555 A1 3/2016 Frankenbach
2016/0090556 A1 3/2016 Frankenbach et al.
2016/0090557 A1 3/2016 Frankenbach et al.
2016/0090558 A1 3/2016 Frankenbach et al.
2016/0092661 A1 3/2016 Hollingshead et al.
2016/0095804 A1 4/2016 Xavier et al.
2016/0095808 A1 4/2016 Okada
2016/0113849 A1 4/2016 Grimadell et al.
2016/0128944 A1 5/2016 Chawrai
2016/0143827 A1 5/2016 Castan Barberan
2016/0193125 A1 7/2016 Jones et al.
2016/0206522 A1 7/2016 Ribaut et al.
2016/0235643 A1 8/2016 Mathonneau et al.
2016/0250115 A1 9/2016 Li et al.
2016/0279048 A1 9/2016 Jayaswal et al.
2016/0287503 A1 10/2016 Schroeder
2016/0287509 A1 10/2016 Peffly
2016/0296656 A1 10/2016 Scavone et al.
2016/0303043 A1 10/2016 Khoury
2016/0306909 A1 10/2016 Hollingshead et al.
2016/0309871 A1 10/2016 Torres Rivera et al.
2016/0310369 A1 10/2016 Thompson et al.
2016/0310370 A1 10/2016 Zhao et al.
2016/0310371 A1 10/2016 Zhao
2016/0310375 A1 10/2016 Torres Rivera
2016/0310386 A1 10/2016 Smith, III et al.
2016/0310388 A1 10/2016 Smith, III et al.
2016/0310389 A1 10/2016 Thompson et al.
2016/0310390 A1 10/2016 Smith, III et al.
2016/0310391 A1 10/2016 Smith, III et al.
2016/0310393 A1 10/2016 Chang et al.
2016/0310402 A1 10/2016 Zhao et al.
2016/0317424 A1 11/2016 Kadir et al.
2016/0326458 A1 11/2016 Smets et al.
2016/0338929 A1 11/2016 Zasloff
2016/0354300 A1 12/2016 Thompson et al.
2017/0066579 A1 3/2017 Zillges
2017/0071837 A1 3/2017 Schelges et al.
2017/0101609 A1 4/2017 Vargas
2017/0110690 A1 4/2017 Lamansky et al.
2017/0110695 A1 4/2017 Nishikawa et al.
2017/0119917 A1 5/2017 Frankenbach et al.
2017/0137752 A1 5/2017 Frankenbach et al.
2017/0137753 A1 5/2017 Frankenbach et al.
2017/0165164 A1 6/2017 Zhao et al.
2017/0165165 A1 6/2017 Zhao et al.
2017/0209359 A1 7/2017 Zhao et al.
2017/0224607 A1 8/2017 Li et al.
2017/0239155 A1 8/2017 Hartnett
2017/0249407 A1 8/2017 Cetti et al.
2017/0249408 A1 8/2017 Cetti et al.
2017/0252273 A1 9/2017 Renock et al.
2017/0255725 A1 9/2017 Frankenbach et al.
2017/0278249 A1 9/2017 Stofel
2017/0283959 A1 10/2017 Shellef
2017/0304172 A1 10/2017 Chang et al.
2017/0304184 A1 10/2017 Glenn, Jr.
2017/0304185 A1 10/2017 Glenn, Jr. et al.
2017/0304186 A1 10/2017 Glenn, Jr.
2017/0326060 A1 11/2017 Matsuo
2017/0333321 A1 11/2017 Carnali
2017/0333591 A9 11/2017 Scavone et al.
2017/0367963 A1 12/2017 Kadir et al.
2018/0044097 A1 2/2018 Zeik
2018/0057451 A1 3/2018 Owens et al.
2018/0066210 A1 3/2018 Frankenbach et al.
2018/0098923 A1 4/2018 Hutton, III
2018/0110594 A1 4/2018 Atkin
2018/0110688 A1 4/2018 Torres Rivera et al.
2018/0110689 A1 4/2018 Torres Rivera et al.
2018/0110690 A1 4/2018 Torres Rivera
2018/0110691 A1 4/2018 Torres Rivera et al.

(56) References Cited

U.S. PATENT DOCUMENTS

2018/0110692 A1 4/2018 Torres Rivera et al.
2018/0110693 A1 4/2018 Renock et al.
2018/0110694 A1 4/2018 Renock et al.
2018/0110695 A1 4/2018 Thompson
2018/0110696 A1 4/2018 Johnson et al.
2018/0110702 A1 4/2018 Constantine et al.
2018/0110704 A1 4/2018 Zhao et al.
2018/0110707 A1 4/2018 Zhao et al.
2018/0110710 A1 4/2018 Zhao et al.
2018/0110714 A1 4/2018 Glenn, Jr. et al.
2018/0116937 A1 5/2018 Park et al.
2018/0116941 A1 5/2018 Wang
2018/0133133 A1 5/2018 Kleinen et al.
2018/0177708 A1 6/2018 Lee et al.
2018/0221266 A1 8/2018 Zhao et al.
2018/0256481 A1 9/2018 Glenn, Jr.
2018/0280270 A1 10/2018 Rughani et al.
2018/0311135 A1 11/2018 Chang
2018/0311136 A1 11/2018 Chang
2018/0318194 A1 11/2018 Hoffmann et al.
2018/0344611 A1 12/2018 Zhao et al.
2018/0344612 A1 12/2018 Zhao et al.
2018/0344613 A1 12/2018 Zhao et al.
2018/0344614 A1 12/2018 Zhao et al.
2018/0360713 A1 12/2018 Jouy et al.
2019/0105242 A1 4/2019 Song
2019/0105243 A1 4/2019 Song
2019/0105244 A1 4/2019 Song
2019/0105245 A1 4/2019 Song
2019/0105246 A1 4/2019 Cochran
2019/0105247 A1 4/2019 Song et al.
2019/0117543 A1 4/2019 Zhao
2019/0117544 A1 4/2019 Zhao
2019/0117545 A1 4/2019 Zhao
2019/0125650 A1 5/2019 Lee et al.
2019/0142711 A1 5/2019 Torres Rivera
2019/0142800 A1 5/2019 Ghosh et al.
2019/0155975 A9 5/2019 Cetti et al.
2019/0167554 A1 6/2019 Wankhade
2019/0183777 A1 6/2019 Gillis
2019/0183778 A1 6/2019 Glenn, Jr.
2019/0192405 A1 6/2019 Zhao
2019/0240121 A1 8/2019 Torres Rivera
2019/0290553 A1 9/2019 Yokogi et al.
2019/0290554 A1 9/2019 Yokogi
2019/0290555 A1 9/2019 Yokogi
2019/0290556 A1 9/2019 Yokogi et al.
2019/0290562 A1 9/2019 Yokogi
2019/0290567 A1 9/2019 Yokogi et al.
2019/0290568 A1 9/2019 Yokogi
2019/0307298 A1 10/2019 Zhao
2019/0307665 A1* 10/2019 Yokogi .................... A61K 8/04
2019/0328647 A1 10/2019 Chang et al.
2019/0365611 A1 12/2019 Brown et al.
2019/0365619 A1 12/2019 Ceballos et al.
2019/0365633 A1 12/2019 Glenn, Jr.
2020/0000690 A1 1/2020 Renock et al.
2020/0078284 A1 3/2020 Botto et al.
2020/0113796 A1 4/2020 Yokogi
2020/0129402 A1 4/2020 Jamadagni
2020/0163846 A1 5/2020 Song
2020/0170894 A1 6/2020 Park et al.
2020/0188243 A1 6/2020 Brown et al.
2020/0197272 A1 6/2020 Hertenstein et al.
2020/0237628 A1 7/2020 Torres Rivera
2020/0281843 A1 9/2020 Comeron
2021/0022986 A1 1/2021 Glenn, Jr.
2021/0093543 A1 4/2021 Parikh et al.
2021/0121385 A1 4/2021 Muller et al.
2021/0128444 A1 5/2021 Muller et al.
2021/0128447 A1 5/2021 Galpin et al.
2021/0169765 A1 6/2021 Renock
2021/0212927 A1 7/2021 Hutton, III et al.
2021/0275410 A1 9/2021 Hutton, III
2021/0315791 A1 10/2021 Springob
2021/0353518 A1 11/2021 Ballhaus et al.
2021/0353522 A1 11/2021 Ballhaus et al.
2021/0401716 A1 12/2021 Gogineni et al.
2022/0062136 A1 3/2022 Feng
2022/0160606 A1 5/2022 Renock
2022/0175640 A1 6/2022 Herteinstein et al.
2022/0257066 A1 8/2022 Brown et al.
2022/0296491 A1 9/2022 Potechin
2022/0323337 A1 10/2022 Yamazaki
2022/0378680 A1 12/2022 Ballhaus et al.
2022/0378684 A1 12/2022 Cochran et al.
2022/0395444 A1 12/2022 Hutton, III
2022/0401327 A1 12/2022 Liu
2023/0053056 A1 2/2023 Renock et al.
2023/0105577 A1 4/2023 Chu

FOREIGN PATENT DOCUMENTS

CA 2078375 A1 3/1994
CN 1286612 A 3/2001
CN 1823929 A 8/2006
CN 100534415 C 9/2009
CN 101112349 B 5/2011
CN 102170854 A 8/2011
CN 101690697 B 10/2011
CN 101559034 B 1/2013
CN 102895151 A 1/2013
CN 102973437 A 3/2013
CN 102697668 B 8/2013
CN 103356408 A 10/2013
CN 102697670 B 7/2014
CN 104107401 A 10/2014
CN 102851015 B 12/2014
CN 105726393 A 7/2016
CN 105769617 A 7/2016
CN 106659664 A 5/2017
CN 106750361 A 5/2017
CN 107595657 A 1/2018
CN 107595673 A 1/2018
CN 107648096 A 2/2018
CN 107737329 A 2/2018
CN 107961212 A 4/2018
CN 108186385 A 6/2018
CN 108283583 A 7/2018
CN 108451858 A 8/2018
CN 110279591 A 9/2019
CN 110960434 A 4/2020
DE 2145204 A1 3/1973
DE 3018456 A1 11/1981
DE 4315396 A1 11/1994
DE 102004012009 A1 9/2005
DE 202005009618 U1 9/2005
DE 102004023720 A1 12/2005
DE 102014225083 A1 10/2015
DE 102014225606 A1 10/2015
DE 102015204987 A1 9/2016
EP 0108517 A2 5/1984
EP 0136914 A2 4/1985
EP 0574086 A2 12/1993
EP 0446094 B1 3/1995
EP 0666358 A1 8/1995
EP 0674898 A2 10/1995
EP 1340485 A2 2/2003
EP 0674898 B2 3/2006
EP 1714678 A1 10/2006
EP 1779838 A1 5/2007
EP 1337231 B1 8/2007
EP 2005939 A1 12/2008
EP 1970045 A3 9/2009
EP 2042216 B1 9/2015
EP 3121210 A1 1/2017
EP 3522858 A1 8/2019
EP 3622946 A1 3/2020
ES 2052450 B1 12/1994
FR 2669531 A1 5/1992
FR 2795955 A1 1/2001
GB 190110699 A 8/1901
GB 191023922 A 10/1911
GB 1347950 A 2/1974

(56) References Cited

FOREIGN PATENT DOCUMENTS

| | | | |
|---|---|---|---|
| GB | 1487812 | A | 10/1977 |
| GB | 2048229 | | 12/1980 |
| GB | 2450727 | A | 1/2009 |
| JP | S56011009 | A | 12/1981 |
| JP | S58113300 | A | 7/1983 |
| JP | S58198412 | A | 11/1983 |
| JP | S60004598 | A | 1/1985 |
| JP | S61236708 | A | 10/1986 |
| JP | S62205200 | A | 9/1987 |
| JP | S63501221 | A | 5/1988 |
| JP | S63165308 | A | 7/1988 |
| JP | H04364114 | A | 12/1992 |
| JP | H06220495 | A | 8/1994 |
| JP | H0753340 | A | 2/1995 |
| JP | H08310924 | A | 11/1996 |
| JP | 09020618 | A | 1/1997 |
| JP | 09030938 | A | 2/1997 |
| JP | H09175961 | A | 7/1997 |
| JP | H10017894 | A | 1/1998 |
| JP | H11139944 | A | 5/1999 |
| JP | 2964226 | B2 | 10/1999 |
| JP | 2000178586 | A | 6/2000 |
| JP | 3069802 | B2 | 7/2000 |
| JP | 2000355519 | A | 12/2000 |
| JP | 2001011492 | A | 1/2001 |
| JP | 2001011497 | A | 1/2001 |
| JP | 2001254099 | A | 9/2001 |
| JP | 2001261529 | A | 9/2001 |
| JP | 2003201217 | A | 12/2001 |
| JP | 2002179552 | A | 6/2002 |
| JP | 2002226889 | A | 8/2002 |
| JP | 2002285191 | A | 10/2002 |
| JP | 2002336337 | A | 11/2002 |
| JP | 2003055699 | A | 2/2003 |
| JP | 2003082398 | A | 3/2003 |
| JP | 2003171688 | A | 6/2003 |
| JP | 2003176497 | A | 6/2003 |
| JP | 2003261413 | A | 9/2003 |
| JP | 2003268398 | A | 9/2003 |
| JP | 3480165 | B2 | 12/2003 |
| JP | 2003342131 | A | 12/2003 |
| JP | 3634988 | B2 | 3/2005 |
| JP | 3634991 | B2 | 3/2005 |
| JP | 3634996 | B2 | 3/2005 |
| JP | 2005187359 | A | 7/2005 |
| JP | 2005232113 | A | 9/2005 |
| JP | 2005239867 | A | 9/2005 |
| JP | 2006063044 | A | 3/2006 |
| JP | 2006104149 | A | 4/2006 |
| JP | 2006124312 | A | 5/2006 |
| JP | 2006183039 | A | 7/2006 |
| JP | 2006193549 | A | 7/2006 |
| JP | 2006249092 | A | 9/2006 |
| JP | 2006282565 | A | 10/2006 |
| JP | 2007131687 | A | 5/2007 |
| JP | 2007177047 | A | 7/2007 |
| JP | 2007223935 | A | 9/2007 |
| JP | 2008001626 | A | 1/2008 |
| JP | 2008214292 | A | 9/2008 |
| JP | 2009096778 | A | 5/2009 |
| JP | 2009120559 | A | 6/2009 |
| JP | 2009161866 | A | 7/2009 |
| JP | 2011153167 | A | 8/2011 |
| JP | 2011190221 | A | 9/2011 |
| JP | 2011241353 | A | 12/2011 |
| JP | 5041113 | B2 | 7/2012 |
| JP | 2013010757 | A | 1/2013 |
| JP | 5220383 | B2 | 3/2013 |
| JP | 2013091641 | A | 5/2013 |
| JP | 2013151434 | A | 8/2013 |
| JP | 2013155143 | A | 8/2013 |
| JP | 2013193968 | A | 9/2013 |
| JP | 2013216639 | A | 10/2013 |
| JP | 6046394 | B2 | 1/2014 |
| JP | 2014009177 | A | 1/2014 |
| JP | 2014024875 | A | 2/2014 |
| JP | 2014037383 | A | 2/2014 |
| JP | 2014091723 | A | 5/2014 |
| JP | 2014234350 | A | 12/2014 |
| JP | 5667790 | B2 | 2/2015 |
| JP | 2015034157 | A | 2/2015 |
| JP | 2015101545 | A | 6/2015 |
| JP | 2015129099 | A | 7/2015 |
| JP | 2016013973 | A | 1/2016 |
| JP | 2016030722 | A | 3/2016 |
| JP | 2016088910 | A | 5/2016 |
| JP | 6184550 | B1 | 8/2017 |
| JP | 2018012673 | A | 1/2018 |
| KR | 100290589 | B1 | 9/2001 |
| KR | 100821846 | B1 | 4/2008 |
| KR | 1020080111280 | A | 12/2008 |
| KR | 20090095359 | A | 9/2009 |
| KR | 20100040180 | A | 4/2010 |
| KR | 20140060882 | A | 5/2014 |
| KR | 101494008 | B1 | 2/2015 |
| KR | 101503922 | B1 | 3/2015 |
| KR | 101532070 | B1 | 7/2015 |
| UA | 50333 | U | 5/2010 |
| WO | 8603679 | A1 | 7/1986 |
| WO | 9114759 | A1 | 10/1991 |
| WO | 91017237 | A1 | 11/1991 |
| WO | 9213520 | A1 | 8/1992 |
| WO | 199325650 | A1 | 12/1993 |
| WO | 9417783 | A2 | 8/1994 |
| WO | 9502389 | A2 | 1/1995 |
| WO | 9714406 | A2 | 4/1997 |
| WO | 9726854 | A1 | 7/1997 |
| WO | 9823258 | A1 | 6/1998 |
| WO | 9906010 | A2 | 2/1999 |
| WO | 9924004 | A1 | 5/1999 |
| WO | 9924013 | A1 | 5/1999 |
| WO | 9957233 | A1 | 11/1999 |
| WO | 0012553 | A1 | 3/2000 |
| WO | 0032601 | | 6/2000 |
| WO | 0108643 | A1 | 2/2001 |
| WO | 0142409 | A1 | 6/2001 |
| WO | 0148021 | A1 | 7/2001 |
| WO | 0195868 | A2 | 12/2001 |
| WO | 2003051319 | A1 | 6/2003 |
| WO | 03096998 | A1 | 11/2003 |
| WO | 2004020526 | A1 | 3/2004 |
| WO | 2004078901 | A1 | 9/2004 |
| WO | 2005023975 | A1 | 3/2005 |
| WO | 2008017540 | A1 | 2/2008 |
| WO | 2008128826 | A1 | 10/2008 |
| WO | 2009016555 | A2 | 2/2009 |
| WO | 2009072027 | A2 | 6/2009 |
| WO | 2010026009 | A1 | 3/2010 |
| WO | 2010052147 | A2 | 5/2010 |
| WO | 2011124560 | A2 | 10/2011 |
| WO | 2012017091 | A2 | 2/2012 |
| WO | 2012052536 | A2 | 4/2012 |
| WO | 2012055587 | A1 | 5/2012 |
| WO | 2012055812 | A1 | 5/2012 |
| WO | 2012084970 | A1 | 6/2012 |
| WO | 2012127009 | A1 | 9/2012 |
| WO | 2012136651 | A1 | 10/2012 |
| WO | 2013010706 | A2 | 1/2013 |
| WO | 2013018805 | A1 | 2/2013 |
| WO | 2013119908 | A1 | 8/2013 |
| WO | 2014014053 | A1 | 1/2014 |
| WO | 2014073245 | A1 | 5/2014 |
| WO | 2014073456 | A1 | 5/2014 |
| WO | 2014111667 | A2 | 7/2014 |
| WO | 2014111668 | A2 | 7/2014 |
| WO | 2014148245 | A1 | 9/2014 |
| WO | 2015085376 | A1 | 6/2015 |
| WO | 2015122371 | A1 | 8/2015 |
| WO | 2016054347 | A1 | 4/2016 |
| WO | 2016067740 | A1 | 5/2016 |
| WO | 2017052161 | A1 | 3/2017 |
| WO | 2017140802 | A1 | 8/2017 |
| WO | 2018023180 | A1 | 2/2018 |
| WO | 2018109148 | A1 | 6/2018 |

(56) References Cited

FOREIGN PATENT DOCUMENTS

WO 2018191573 A1 10/2018
WO 2019030458 A2 2/2019
WO 2020076881 A1 4/2020

OTHER PUBLICATIONS

"Foam & chemical contamination in waterways", Retrieved From https://www.epa.nsw.gov.au/-/media/epa/corporate-site/resources/epa/foam-chemical-contamination-in-waterway.pdf, Dec 2015, 2 Pages.
"Hydrating Conditioner Bar" Mintel Database, www.gnpd.com, Aug. 1, 2018, 4 Pages.
"Jaguar® Optima", Solvay, site: www.solvay.com, year 2023, 1 page.
"Natural Detangling Shampoo", Mintel Database, dated Sep. 13, 2017; 2 pages.
"Personal care solutions Guide", Solvay, Publication date: May 2018, 84 pages.
"Soda Shampoo", Mintel Database, dated Apr. 2015; pp. 1-4.
"Treatment Foam for Recurrent Scaling Conditions", Mintel Database, Aug. 2007; pp. 1-2.
AA01317 PCT Search Report and Written Opinion for PCT/US2019/055284 dated Jan. 22, 2020, 15 pages.
Acne Foaming Cleanser, Database accession No. 4172863, Jul. 29, 2016, 3 pages.
Air Quality of the Iowa Department of Natural Resources. A Review of the Science and Technology of Odor Measurement, 2005, 51 pages.
All Office Actions; U.S. Appl. No. 16/595,755, filed on Oct. 8, 2019.
All Office Actions; U.S. Appl. No. 16/441,618, filed Jun. 14, 2019.
All Office Actions; U.S. Appl. No. 16/441,639, filed Jun. 14, 2019.
All Office Actions; U.S. Appl. No. 16/441,671, filed Jun. 14, 2019.
Anonymous, "Healing + Anti-Breakage Shampoo", ID# 3383875, Mintel GNPD, URL: http://www.gnpd.com, dated Aug. 2015, 3 pages.
Anonymous, "Medicated Cleanser", Nioxin Research Laboratories, Mintel GNPD [online], ID:1060983, URL: http://www.gnpd.com, dated Feb. 2009, 4 pages.
Anonymous, "Shampoo", ID# 1743027, Mintel GNPD, URL: http://www.gnpd.com, dated Mar. 2012, 3 pages.
Anonymous: "MERQUAT Polyquaternium 47 Series, Water Soluble Polymers for Personal Care", Jul. 30, 2017, URL: https://www.in-cosmetics.com/_novadocuments/2729, retrieved on Dec 21, 2018 ; 1 page.
Anonymous: "Anti-Dandruff Scalp Care Shampoo", MINTEL, Database accession No. 301924, Sep. 16, 2004, 2 pages.
Anonymous: "Anticaspa-Graso Anti-Dandruff Shampoo", Database GNPD [Online] Mintel; XPC:155787029, Database accession No. 351776paragraph [ingredients], Apr. 5, 2005, 2 Pages.
Anonymous: "Naturally Derived Body Wash", Database GNPD [Online] MINTEL; Feb. 15, 2021, 2 pages.
Anonymous: "Peptide Shampoo", Database GNPD [Online] MINTEL; Dec 14, 2015, 3 pages.
Anonymous: "Replenishing Moisture Shampoo", Database GNPD [Online] MINTEL, Mar. 10, 2015, 3 Pages.
Anonymous: "Shampoo", Database GNPD [Online] MINTEL, Jan. 26, 2021, 3 pages.
Anonymous: "Shampooing au Phytolait d'abricot—Formule N°102-MP06-MI3-AA03", Internet Citation, Retrieved from the Internet: URL: http://web.archive.org/web/20050219040350/www.albanmuller.com/francais/catalogue/formules/formul10.asp, Feb. 19, 2005, 1 page.
Anonymous; "Shampoo", ID: 7162235, Database GNPD [Online] MINTEL; dated Jan. 6, 2020, 3 pages.
ASTM D3954-94, Reapproved 2010, vol. 15.04, Standard Test Method for Dropping Point of Waxes., 2 pages.
BASF, "Practical Guide to Rheology Modifiers", download from https://insights.basfcom/files/BASF_ED_RheologyModifiers_download.pdf on Nov. 1, 2022, 15 Pages.
Brattoli et al. Odour Detection Methods: Olfactometry and Chemical Sensors. Sensors (Basel), 2011; 11(5); pp. 5290-5322.
Cafasso, "What's the proper order to use shampoo and conditioner while bathing", Healthline, Retrieved from Internet: https://www.healthline.com/health/beauty-skin-care/shampoo-or-conditioner-first, dated Jul. 13, 2020, 2 pages.
Carbopol Aqua SF-1 Polymer Technical Data Sheet, TDS-294, dated Dec. 2000 ; pp. 1-9.
Chemical Book, Isolongifolone, available at http://www.chemicalbook.com/ProductChemicalPropertiesCB5318980_EN.htm, Copyright 2016, 1 page.
Christensen et al., "Experimental Determination of Bubble Size Distribution in a Water col. by Interferometric Particle Imaging and Telecentric Direct Image Method", Student Report, Aalborg University; dated Jun. 3, 2014; 123 pages.
Crepaldi, E.L., et al., Chemical, Structural, and Thermal Properties of Zn(II)—Cr(III) Layered Double Hydroxides Intercalated with Sulfated and Sulfonated Surfactants, Journal of Colloid and Interface Science, vol. 248, 2002, pp. 429-442.
CTFA Cosmetic Ingredient Dictionary, 1982, 3rd Edition, The Cosmetic, Toiletry & Fragrance Association, Inc., Washington, DC, 1982.
D'Souza et al., Shampoo and Conditioners: What a Dermatologist Should Know? Indian J Dermatol, 60(3), 2015, pp. 248-254.
Database GNPD [Online] MINTEL; ,anonymous: Dandruff Control Shampoo 11, XP055787038, Database accession No. 5556267, abstract, Mar. 28, 2018, 2 Pages.
Database WPI; Week 201459; Thomson scientific, London, GB; AN 2014-P66521; XP002752638; (No known date), 2 pages.
Datasheet: Empigen Total Active TC/U, Datasheet, dated (Innospec), Jan. 31, 2017, 2 pages.
Dehyquart Guar: Published dated Nov. 2010 ; pp. 1-34.
Duis et al., "Environmental fate and effects of water-soluble synthetic organic polymers used in cosmetic products", Enviromental Sciences Europe, 33:21, 2021; 20 pages.
Fevola, Michael J. "Guar Hydroxypropyltrimonium Chloride." Cosmetics and toiletries; vol. 127.1; Jan. 2012 ; pp. 16-21.
Grillet et al., "Polymer Gel Rheology and Adhesion", Rheology, 2012, pp. 59-80.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018; p. 1.
Happi: "Sulfate-Free Surfactants Conditioning Shampoo", Retrieved from the Internet: URL:https://www.happi.com/contents/view_formulary/2009-10-01/sulfate-free-surfactants-conditioning-shampoo/, XP002804301, Jan. 10, 2019, 1 page.
Inspection certificate for Hostapon® CCG, Clariant Iberica Production, S.A., May 6, 2019; p. 1-2.
Matsouka et al., "Vesicle formation of disodium lauryl sulfosuccinate", Journal of Molecular Liquids, 348, 118422, Nov. 1, 2021, 7 pages.
Mcginley et al., "Performance Verification of Air Freshener Products and Other Odour Control Devices for Indoor Air Quality Malodours", Presented at the 8th Workshop on Odour and Emissions of Plastic Materials Universitat Kassel Institut for Wesrkstofftechnik Kassel, Germany, 2006, 13 pages.
Mcginley et al., American Association of Textile Chemists and Colorists, 2017, 16 pages.
Medvedev, Diffusion Coefficients in Multicomponent Mixtures, PhD Thesis from Technical University of Denmark, dated 2005, 181 pages.
Mintel GNPD Base, Bright Blonde Shampoo Record No. 3412889 Feb. 29, 2016 ; 2 pages.
Mintel GNPD Base, Mineral Conquer Blonde Silver Shampoo Record No. 3953107 Apr. 30, 2016; 2 pages.
Mintel GNPD Base, Royal Treatment Collection, Record No. 1946223 dated Dec. 31, 2011, 3 pages.
Morioka, H. et al. "Effects of Zinc on the New Preparation Method of Hydroxy Double Salts" Inorg. Chem., 38, 1999, pp. 4211-4216.
Musazzi, "Emulsion versus nonoemulsion: how much is the formulative shift critical for a cosmetic product?" (Drug Deliv. and Trans. Res. (2018) 8: pp. 414-421.

(56) References Cited

OTHER PUBLICATIONS

Natural oils: why specific carbon chains are chosen for certain surfactant properties, Chemlink, URL Link: https://www.chemlink.co.uk/natural-oils-why-specific-carbon-chains-are-chosen-for-certain-surfactant-properties/a, 2022, 4 Pages.
Naturally Rich Moisturizing Shampoo, Database accession No. 6421011, Mar. 27, 2019, 3 pages.
Noritomi H. Formation and Solubilization Property of Water-in-Oil Microemulsions of Alkyl Glucoisdes. Advances in Nanoparticles, 2013, 2, pp. 366-371.
P. A. Cornwell, "A review of shampoo surfactant technology: consumer benefits, raw materials and recent developments", International Journal of Cosmetic Science, 40 , Oct. 27, 2017, pp. 16-30.
Parchem fine & specialty chemicals. MIPA-laureth sulfate supplier distributor—CAS 83016-76-6; dated 2021; pp. 1-7.
PERM Inc, , Diffusion Coefficient: Measurement Techiques, https://perminc.com/resources/fundamentals-of-fluid-flow-in-porous-media/chapter-3-molecular-diffusion/diffusion-coefficient/measurement-techniques, dated Oct. 2020; p. 1-4.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-the Safety-Assessment-of-Polyquaternium-10.pdf, retrieved on Dec 20, 2018; 9 pages.
Practical Modern Hair Science, Published 2012; 43 pages.
Product Bulletin, Amphosol® CG, Cocamidopropyl Betaine, Stepan Company, Jun. 2011; 1-2 pages.
Product Data Record Tego® Betain F KB 5, dated Jul. 1, 2015, 4 pages.
Product Data Sheet for Chemoryl™ LS Surfactant, Sodium Lauroyl Sarcosinate, Lubrizol Advanced Materials, Inc, Mar. 24, 2020; 1-2 pages.
Product Data Sheet, Eversoft™ UCS-40S, Disodium Cocoyl Glutamate (Sodium Cocoyl Glutamate*), Sino Lion USA, Jul. 2018; 2 pages.
Product Fact Sheet—Hostapon® CCG, mild anionic surfactant for the cosmetic industry, Clariant International Ltd., Aug. 2014 ; 1-3 pages.
Product Fact Sheet, Hostapon® CGN, Mild anionic surfactant for the cosmetic industry, Clariant International Ltd., Jan. 2016; 1-2 pages.
PubChem CID 3033856 for decyl glucoside. downloaded Jun. 22, 2023, 32 pages.
Rajendran A. et al: "Study on the Analysis of Trace Elements in Aloe veraand Its Biological Importance Study on the Analysis of Trace Elements in Aloe vera and Its Biological Importance", Journal of Applied Sciences Research, Jan. 1, 2007, pp. 1476-1478.
Ramachandra et al., "Processing of Aloe Vera Leaf Gel: A Review", American Journal of Agricultural and Biological Sciences 3 (2), 2008, pp. 502-510.
Robinson et al., Final Report of the Amended Safety Assessment of Sodium Laureth Sulfate and Related Salts of SulfatedEthoxylated Alcohols, International Journal of Toxicology 29 (Supplement 3); dated 2010; pp. 1515-1615.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, dated Nov. 1, 2008, pp. 304-308, p. 305.
Safety assessment of amino acid alkyl amides used in cosmetics , dated Sep. 20, 2013, 46 pages.
Sbhatu et al., "Formulation and Physicochemical Evaluation of Lab-Based Aloe adigratana Reynolds Shampoos", Hindawi, International Journal of Analytical Chemistry, vol. 2020, Article ID 6290617, URL: https://www.ncbi.nlm.nih.gov/pmc/articles/PMC7160718/, Apr. 4, 2020, 7 pages.
Schaefer, Katie, "Eco-friendly, Non-flammable Liquified Gas Propellant", https://www.cosmeticsandtoiletries.com/formulating/function/aids/138418589.html#close-olyticsmodal., Jan. 30, 2012, 1-2 pages.
Sensory.,"A Review of The Science and Technology of Odor Measurement", Prepared for the Air Quality Bureau of the lowa Department of Natural Resources, Dec. 30, 2005 51 pages.
Shampoo C, Database accession No. 1632217, Sep. 29, 2011, 3 pages.
Shampoo Manufacturing Plant, Lodha International, URL: https://www.lodhapharma.com/shampoo-manufacturing-plant.php#:~:text=Shampoos%20are%20categorized%20as%20viscous,if%20not%20all%20of%20them, 2018, 4 pages.
Shampoo, ID# 6148479, Mintel GNPD [online], URL: http://www.gnpd.com, Nov. 2018, 4 pages.
Softazoline CL-R, Kawaken Singapore PTE Ltd. Website printout from http://kawaken.com.sg/softazoline-ch-r//a, accessed on Nov. 30, 2022.
Technical Information; TEGO® Betain F KB 5 / TEGO® Betain F KM 1; Mild amphoteric surfactants: www.evonik.com/personal-care; Jul. 2010; 2 pages.
Todd et al., Volatile Silicone Fluids for Cosmetics, Cosmetics and Toiletries, vol. 91, pp. 27-32.
UL Prospector® Product Data Sheet, Plantacare® 818 UP, C8-16 fatty alcohol glucoside, BASF, dated May 21, 2015; 1-3 pages.
Unhale Shrikrushna Subhash et al: Formulation and Development of Sulphate Free Shampoo About an Updates and Guidelines of Corona Virus View project health and beauty science View project Rohit Bhavsar Reliance Industries Limited; International Journal for Research inApplied Science & Engineering Technology, XP055842327, No Known Date, 14 pages.
Yang et al., "Synthesis and foaming performance of Lauramidopropyl Betaine Derivate Surfactants", Materials Science Forum, vol. 953, Jan. 9, 2019, 1 page.
"Deep Image Matting", Ning Xu et al., Beckman Institute for Advanced Science and Technology, University of Illinois at Urbana-Champaign, Adobe Research, dated Mar. 10, 2017; 10 pages.

* cited by examiner

PERSONAL CARE PRODUCT CUSTOMIZED BY DISCRETE PARTICLES AND METHOD OF APPLY THEREOF

FIELD OF THE INVENTION

The present disclosure is directed generally to a relatively large solid particle comprising a surfactant and a high melting point fatty compound. More specifically, the present disclosure relates to a relatively large hair conditioning particle comprising a specific cationic surfactant, fatty compound and benefit agent.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits.

For example, United States Patent Application Publication No. 2003/0103923 from SAN-EI KAGAKU relates to a composition containing an alcohol, the composition being for blending in a hair treatment agent, and hair conditioners prepared from the hair treatment agents. SAN-EI publication discloses a variety of such compositions for blending in hair treatment agents, including compositions containing fatty alcohols and cationic surfactants, for example, in Examples 100-110. The SAN-EI publication also discloses hair conditioners by using such compositions for blending, for example, in Example 112-118.

In Examples 112-117 of the SAN-EI publication, the compositions for blending (Examples 102, 103, 104 and 106) are heated up to 80° C. or more, then mixed with mainly water to make hair conditioners. The compositions for blending (Examples 102, 103, 104 and 106) used therein contain higher percentages of liquid material (for example, 27% propylene glycol in Example 102, 47% of liquid petrolatum in Example 103, 43% of glycerin and 18% of liquid petrolatum in Example 104, and 28% of glycerin in Example 106) together with fatty alcohols and cationic surfactants.

In Example 118 of the SAN-EI publication, a composition for blending (Example 111) is added to an emulsion cooled down below 40° C., wherein the emulsion is of water and an additive composition containing a cationic surfactant and a fatty alcohol, and further mixed with water to make hair conditioner. The composition for blending (Example 111) contains ethanol, cationic surfactant, and more than 80% of water, and no fatty alcohols.

SAN-EI publication also discloses preparation of hair conditioners in Examples 150-156. In Example 150-154, compositions for blending (Examples 123, 126, 127, 130, 133, and 134) are heated to above 80° C., and added to water which is also heated to above 80° C., and emulsified and cooled to make hair conditioners. The compositions for blending (Examples 123, 126, 127, 130, 133, and 134) contain cationic surfactants and fatty alcohols, and also 15-20% of liquid oils (in Examples 123, 130 and 133) or 6-8% of polyoxyethylene esters (in Examples 126, 127 and 134).

Another example can be United States Patent Application Publication No. 2003/223952 from P&G relating to a process for preparing cleansing composition comprising (a) combining a fatty alcohol and a surfactant in a premix at a temperature sufficient to allow partitioning of the surfactant into the fatty alcohol, (b) cooling the mixture below the chain melt temperature of the premix to form a gel network, (c) adding the gel network to a detersive surfactant and an aqueous carrier to form a cleansing composition. The P&G publication discloses Examples in paragraphs [0186]-[0190], using such gel network containing fatty alcohol and cationic surfactant.

Also, United States Patent Application Publication No. 2016/143827 from Kao discloses a composition that is solid at room temperature and wherein the water content is 10 wt % or less, and a hair conditioner composition prepared by dispersing the solid composition in water at moderate temperatures. European Patent Application Publication No. 2394632 from Shiseido discloses a hair conditioner composition with an extremely low water content, and from which a hair conditioner composition can easily be manufactured simply by diluting with water.

However, there remains a need to provide customized personal care composition to provide at least one of the following benefits:

- Boosting rheology especially storage modulus (G') and/or boosting rich conditioning perception/feeling, preferably independently from the use of thickening polymer.
- Boosting conditioning benefits
- Adding a new benefit such as aesthetic benefit, anti-dandruff benefit, sensate such as heating/cooling, and scent
- Providing at least one of the above benefits, while having improved stability especially when containing incompatible components and/or while not causing negative interaction with personal care composition, package, and any other environmental factors.

None of the existing art provides all of the advantages and benefits of the present invention.

SUMMARY OF THE INVENTION

Disclosed herein is a solid, discrete hair conditioning particle, comprising a cationic surfactant, a fatty compound and a benefit agent. The cationic surfactant is selected from mono-long alkyl quaternized ammonium salts, a combination of mono-long alkyl quaternized ammonium salts and di-long alkyl quaternized ammonium salts, mono-long alkyl amines, and a combination of mono-long alkyl amines and di-long alkyl quaternized ammonium salts. The high melting point fatty compound is selected from fatty alcohols, fatty acids, fatty alcohol derivatives, fatty acid derivatives, and mixtures of these. The benefit agent is selected from silicone compounds, perfumes, aesthetic benefit agents, sensate agents, anti-dandruff agents, incompatible agents and mixtures of these. The hair conditioning particle has a particle size of about 50 micrometers to about 2000 micrometers.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

Product with Usage Instruction/Method to Applying Customized Personal Care Composition The personal care product of the present invention comprises:

- one or more solid discrete particles of a mixture composition, wherein the mixture composition comprises a surfactant and a high melting point fatty compound, and wherein the mixture composition contains less than about 50% of water; and
- a container containing the discrete particles;
- a usage instruction comprising depiction corresponding to the following steps:
- (i) mixing an aqueous personal care composition and the solid discrete particles to make a customized personal care product; and
- (ii) applying the customized personal care product to a targeted surface.

In the present invention, it is preferred that the instruction is free of:

- depiction corresponding to a step to any of the discrete particle, the aqueous personal care composition and the customized personal care product; and/or
- depiction make the temperature of any of the discrete particle, the aqueous personal care composition and the customized personal care product to exceed 65° C., more preferably 60° C., still more preferably 55° C., even more preferably 50° C., further preferably 45° C.

In the present invention, it is preferred that the instruction further comprises:

- depiction to restrict to heat any of the discrete particle, the aqueous personal care composition and the customized personal care product; and/or
- depiction to restrict that the temperature of any of the discrete particle, the aqueous personal care composition and the customized personal care product to exceed 65° C., more preferably 60° C., still more preferably 55° C., even more preferably 50° C., further preferably 45° C.

The method of the present invention is that of applying a customized personal care product comprising the following steps:

- (i) Mixing an aqueous personal care composition and one or more solid discrete particles of a mixture composition to make a customized personal care product, wherein the mixture composition comprises a surfactant and a high melting point fatty compound, and wherein the mixture composition contains less than about 50% of water; and
- (ii) Applying the customized personal care product to a target surface.

In the present invention, it is preferred that the method is free of a step to make the temperature of any of the discrete particle, the aqueous personal care composition and the customized personal care product to exceed 65° C., more preferably 60° C., still more preferably 55° C., even more preferably 50° C., further preferably 45° C.

The usage instruction may further comprise depiction corresponding to the following step to wait for from about 1 min to about 1 day after mixing and before applying the customized personal care composition to hair, preferably from about 1 minute to about 1 night, more preferably from about 1 minute to about 3 hours, still more preferably from about 1 min to about 1 hour after mixing and before applying. The method of applying the customized personal care composition may further comprise the above step.

The usage instruction may further comprise depiction for suggesting an usage amount of the solid discrete particles, for example, from about 0.1 g to about 10 g of the solid discrete particles for 100 ml of the personal care composition, preferably from about 0.1 g to about 7 g, more preferably from about 0.1 g to about 5 g of the solid discrete particles for 100 ml of the personal care composition, alternatively, one container of the solid discrete particles for 1 bottle of the personal care composition. The above usage amount can be also applied in the method of applying the customized personal care composition.

The customized personal care product is applied to a targeted surface. The targeted surface is an appropriate portion selected from hair, body and/or face, depending on the type of the products and/or compositions.

Aqueous Personal Care Composition

The aqueous personal care composition to be mixed with the solid discrete particles is preferably:

- selected from the group consisting of a hair care composition, a body care composition, a facial skin care composition, and mixtures thereof, preferably a hair care composition;
- the one which a user has or buy; and/or
- substantially free of a detersive surfactant selected from anionic surfactants, zwitterionic surfactant, amphoteric surfactant, and combinations thereof.

The usage instruction may further comprise depiction corresponding to at least one of these aspects, or all of these aspects independently or concurrently.

In the present invention, "the composition being substantially free of detersive surfactants" means that: the composition is free of detersive surfactants; or, if the aqueous personal care composition contains detersive surfactants, the level of such detersive surfactants is very low. In the present invention, a total level of such detersive surfactants, if included, preferably 0.1% or less, more preferably 0.05% or less, still more preferably 0.01% or less by weight of the aqueous personal care composition. Most preferably, the total level of such detersive surfactants is 0% by weight of the composition.

The aqueous personal composition comprises an aqueous carrier. Aqueous carrier useful in the present invention includes water and water solutions of lower alkyl alcohols. The lower alkyl alcohols useful herein are monohydric alcohols having 1 to 6 carbons, more preferably ethanol and isopropanol. Preferably, the aqueous carrier is substantially water. Deionized water is preferably used. Water from natural sources including mineral cations can also be used, depending on the desired characteristic of the product. Generally, the aqueous carrier can be contained in the personal care compositions at a level of q.s. to 100% of the composition, preferably from about 40% to about 99%, more preferably from about 50% to about 95%, still more preferably from about 70% to about 95%, even more preferably from about 80% to about 95% by weight of the composition.

Preferably the aqueous personal care composition comprises at least one of the following: a cationic surfactant, a nonionic surfactant, a polymer, and mixtures thereof, more preferably a cationic surfactant, still more preferably a cationic surfactant and high melting point fatty compound. The polymer can be a water soluble polymer such as water soluble thickening polymer and/or water soluble styling polymer Water Soluble Polymer The aqueous personal care composition can include, for example, from about 0.005% to about 10%, preferably from about 0.01% to about 5%, more preferably from about 0.05% to about 5%, still more preferably from about 0.1% to about 5%, and even more preferably from about 0.2% to about 3% of the water soluble polymers, by weight of the aqueous personal care composition.

The water soluble polymers may have solubility in water, measured at 25° C., of from about 0.1 g/L to about 500 g/L. The water soluble polymers may be of synthetic or natural origin and may be modified by means of a chemical reaction.

In an embodiment, the water soluble polymers may have a weight average molecular weight of from about 5,000 g/mol to about 50,000,000 g/mol, alternatively from about 10,000 g/mol to about 10,000,000 g/mol, alternatively from about 20,000 g/mol to about 5,000,000 g/mol, and alternatively from about 100,000 g/mol to about 3,000,000 g/mol.

In an embodiment, the aqueous personal care composition with the water soluble polymers may have a viscosity at 20° C. of from about 100 centipoise to about 10,000,000 centipoise, alternatively from about 500 centipoise to about 5,000,000 centipoise, and alternatively from about 1000 centipoise to about 100,000 centipoise.

The water soluble polymer can be nonionic, cationic, anionic, amphoteric, and preferably nonionic or cationic especially when the surfactant contained in the discrete particle is nonionic or cationic.

Non-limiting examples of synthetic water soluble polymers may be selected from the group consisting of polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, polyurethanes, polycarboxylic acids, polyvinyl acetates, polyesters, polyamides, polyamines, polyethyleneimines, and PEG-240/HDI COPOLYMER BIS-DECYLTETRADECETH-20ETHER.

Further non-limiting examples of synthetic water soluble polymers may be selected from the group consisting of copolymers of anionic, cationic and amphoteric monomers and mixtures thereof, including maleic acrylate based copolymers, maleic methacrylate based copolymers, copolymers of methylvinyl ether and of maleic anhydride, copolymers of vinyl acetate and of crotonic acid, copolymers of vinylpyrrolidone and of vinyl acetate, and copolymers of vinylpyrrolidone and of caprolactam, polyquaternium-37, polyquaternium-6 and polyquaternium-7.

Non-limiting examples of natural water soluble polymers may be selected from the group consisting of karaya gum, tragacanth gum, gum arabic, acemannan, konjac mannan, acacia gum, gum ghatti, whey protein isolate, soy protein isolate, guar gum, locust bean gum, quince seed gum, psyllium seed gum, carrageenan, alginates, agar, fruit extracts (pectins), xanthan gum, gellan gum, pullulan, hyaluronic acid, chondroitin sulfate, and dextran, casein, gelatin, keratin, keratin hydrolysates, sulfonic keratins, albumin, collagen, glutelin, glucagons, gluten, zein, shellac, and mixtures thereof.

Non-limiting examples of modified natural water soluble polymers may be selected from the group consisting of (1) cellulose derivatives including hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose, cellulose ethers, cellulose esters; and (2) guar derivatives including hydroxypropyl guar. Suitable hydroxypropylmethylcelluloses may include those available from the Dow Chemical Company (Midland, MI).

Among them, highly preferred are, Polyquaternium-37 and PEG-240/HDI COPOLYMER BIS-DECYLTETRADECETH-20ETHER.

Container

Materials, structures, and shapes of the container can be anything as long as the container can contain the solid discrete particles therein and can dispense the solid discrete particles there from, and has reasonable protection from water.

The structure and the shape can be varied, for examples, for containers for a single dose in which the solid discrete particles are contained at a relatively smaller amount, or for containers for multiple doses in which the solid discrete particles are contained at relatively larger amount.

Solid Discrete Particle

Solid discrete particles of a mixture composition are used herein. The solid discrete particle preferably comprises 100% of the mixture composition, i.e., consisting of the mixture composition. When the discrete particles contain water before swelling, it is preferred to control the level of the water before swelling, so that the discrete particle before swelling contains less than about 50% of water, more preferably less than about 25%, still more preferably less than about 15%, even more preferably less than about 10%, further preferably less than about 8% of water, by weight of the discrete particle.

The solid discrete particles in the container are preferably dry and contained without any liquid carrier suspending the discrete particles.

The solid discrete particle preferably has a particle size of from about 1 micrometer to about 2000 micrometers, more preferably from about 10 micrometers to about 1000 micrometers, still more preferably from about 50 micrometers to about 500 micrometers.

The solid discrete particles herein can be in any shape, for example, spherical shape, rectangular shape, or diamond shape.

Preferably, the discrete particles useful herein are dispersed in the personal care composition and can be observed as discrete particles in final product visually, for example, by microscope, however, those do not show maltese cross sign when measured by polarized light microscopy. This means that the discrete particles useful herein are not vesicles which are often seen in emulsions comprising surfactants, high melting fatty compounds and aqueous carrier. Generally, surfactants, high melting fatty compounds and aqueous carrier form emulsions, preferably a gel matrix. In such emulsions and gel matrix, these components often form lamellar vesicle and/or lamellar sheet. Such Lamellar vesicle can be observed as discrete particle by microscope, however, shows maltese cross sign when measured by polarized microscope.

Preferably, the discrete particles useful herein are swollen in the aqueous personal care composition, more preferably swollen by aqueous carrier contained in the aqueous personal care composition, still more preferably by water contained in the aqueous personal care composition.

Before and after swelling, the discrete particle is preferably not an oil-in-water emulsion or water-in-oil-in-water emulsion, more preferably, not any emulsion including water-in-oil emulsion and oil-in-water-in-oil emulsion.

The discrete particle herein is different from particles coated or encapsulated by, for example, polymers.

The discrete particle useful herein is different from swellable silicone elastomer and swellable thickening polymer. Preferably, the discrete particle and the mixture composition are substantially free of such swellable silicone elastomer and swellable thickening polymer. In the present invention, "the discrete particle and the mixture composition being substantially free of swellable silicone elastomer and swellable thickening polymer" means that: the discrete particle and the mixture composition are free of swellable silicone elastomer and swellable thickening polymer; or, if the discrete particle and the mixture composition contains swellable silicone elastomer and swellable thickening polymer, the level of such swellable silicone elastomer and swellable thickening polymer is very low. In the present invention, a total level of such swellable silicone elastomer and swellable thickening polymer, if included, preferably 0.1% or less, more preferably 0.05% or less, still more preferably 0.01% or less by weight of the discrete particle or by the weight of the mixture composition. Most preferably, the total level of such swellable silicone elastomer and swellable thickening polymer is 0% by weight of the discrete particle or by the weight of the mixture composition.

The solid discrete particles may be swollen and/or dissolved faster in aqueous composition, when the solid discrete particle and the mixture composition contains liquid polypropylene glycol and/or di-long alkyl cationic surfactant such as di-long alkyl quaternized ammonium salt.

Mixture Composition

The mixture composition useful herein comprises a surfactant and a high melting point fatty compound. The mixture composition may further contain a benefit agent. These ingredients are explained later in detail.

The surfactants and the high melting point fatty compounds are present in the mixture composition, with or without other ingredients, at a level by weight of the mixture composition of, preferably from about 10% to about 100%, more preferably from about 20% to about 100%, still more preferably from about 40% to about 100%, even more preferably from about 60% to about 100%, further more preferably from about 80% to about 100%, in view of having solid discrete particles of the mixture composition Other than the surfactants and high melting point fatty compounds, when the mixture composition contains any liquid such as water-insoluble, water-miscible, and water-soluble liquids and water, it is also preferred to control the level of such liquids, so that the total liquid level in the mixture composition can be preferably up to about 50%, more preferably up to about 40%, still more preferably up to about 30% by weight of the mixture composition, in view of having solid discrete particle of the mixture composition.

When the liquid is water insoluble liquid such as silicones, such water insoluble liquid can be contained in the mixture composition at a level by weight of the mixture composition of preferably up to about 50%, more preferably up to about 40%, still more preferably up to about 30%.

When the liquid is water miscible liquid such propylene glycol and glycerin, such water miscible liquid can be contained in the mixture composition at a level by weight of the mixture composition of preferably up to about 50%, more preferably up to about 40%, still more preferably up to about 30%.

When the liquid is water soluble liquids such as isopropylalcohol (IPA) and ethanol, such water soluble liquid can be contained in the mixture composition at a level by weight of the mixture composition of preferably up to about 50%, more preferably up to about 30%, still more preferably up to about 20%.

When the mixture composition contains water, it is preferred to control the level of the water so that the mixture composition contains less than about 50% of water, more preferably less than about 25%, still more preferably less than about 15%, even more preferably less than about 10%, further preferably less than about 8% of water, by weight of the mixture composition, in view of having solid discrete particle of the mixture composition.

Preferably in the mixture composition, the surfactant and the high melting point fatty compound are contained at a level such that the weight ratio of the surfactant to the high melting point fatty compound is in the range of from about 1:1 to about 1:10, more preferably from about 1:1 to about 1:4, still more preferably from about 1:2 to about 1:4, in view of boosting rheology and/or conditioning benefit.

Surfactant for the Mixture Composition

The surfactant used for the mixture composition is preferably hydrophobic, and is also preferably selected from the group consisting of: a cationic surfactant, a nonionic surfactant, and mixtures thereof; and still more preferably a cationic surfactant. Such preferred cationic surfactants are further explained below under the title "CATIONIC SURFACTANT".

High Melting Point Fatty Compound for the Mixture Composition

The high melting point fatty compound used for the mixture composition is explained below under the title "HIGH MELTING POINT FATTY COMPOUND".

Benefit Agent for the Mixture Composition

The mixture composition may further comprise a benefit agent in addition to the surfactant and the high melting point fatty compound, which are different from the surfactant and the high melting point fatty compound. This benefit agent is also different from the aqueous carrier and water which may be contained in the mixture composition.

The benefit agent can be contained in the mixture composition at a level by the weight of the mixture composition, of preferably from about 0.1% to about 90%, more preferably from about 0.3% to about 60%, still more preferably from about 0.5% to about 40%, even more preferably from about 0.5% to about 30% in view of providing benefits from the benefit agents and in view of having discrete particle of the mixture composition.

Preferably, such benefit agent is selected from the group consisting of: silicone compounds; perfumes; aesthetic benefit agents such as coloring agents to add a different color to the discrete particle from the color of the aqueous personal care composition; sensate agents such as heating/cooling agents; anti-dandruff agents; incompatible agents which are incompatible to at least one of personal care composition, package, and any other environmental factors; and mixtures thereof.

Such silicone compounds are further explained below under the title "SILICONE COMPOUND".

Such perfumes can be anything, for example, perfume per se, and perfume micro capsule (PMC) in which perfume is encapsulated by a polymeric outer layer.

Such coloring agent can be anything, for example, pigments and dyes.

Such incompatible agents are, for example, those selected from the group consisting of:

solid minerals or chemical substances that have high ionic strength and/or high surface charge and tend to cause agglomeration and/or crystallization in aqueous compositions, which are, for example, mica, salicylic acid, and metal pyrithione such as zinc pyrithione with or without ionic polymer coating or dispersion;

organic oil material which is highly interactive with gel network component, for example, hexyldecanol, isostearyl isostearate and mixtures thereof.

Depending on the type of the benefit agent, when containing the benefit agent, the solid discrete particles may provide at least one of the following:

Boosting rheology especially storage modulus (G') and/or boosting rich conditioning perception/feeling, preferably independently from the use of thickening polymer.

Boosting conditioning benefits

Adding a new benefit such as aesthetic benefit, anti-dandruff benefit, sensate such as heating/cooling, and scent Providing at least one of the above benefits, while having improved stability especially when containing incompatible components and/or while not causing negative interaction with personal care composition, package, and any other environmental factors.

Cationic Surfactant

Cationic surfactant useful herein can be one cationic surfactant or a mixture of two or more cationic surfactants. Preferably, the cationic surfactant is selected from: mono-long alkyl quaternized ammonium salt; a combination of mono-long alkyl quaternized ammonium salt and di-long alkyl quaternized ammonium salt; mono-long alkyl amine; a combination of mono-long alkyl amine and di-long alkyl quaternized ammonium salt.

Mono-Long Alkyl Quaternized Ammonium Salt

The mono-long alkyl quaternized ammonium salts useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

(I)

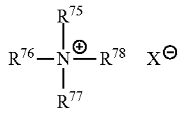

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-Long Alkyl Quaternized Ammonium Salts

When used, di-long alkyl quaternized ammonium salts are preferably combined with a mono-long alkyl quaternized ammonium salt or mono-long alkyl amine salt, at the weight ratio of from 1:1 to 1:5, more preferably from 1:1.2 to 1:5, still more preferably from 1:1.5 to 1:4, in view of stability in rheology and conditioning benefits.

Di-long alkyl quaternized ammonium salts useful herein are those having two long alkyl chains of from 12 to 30 carbon atoms, more preferably from 16 to 24 carbon atoms, still more preferably from 18 to 22 carbon atoms. Such di-long alkyl quaternized ammonium salts useful herein are those having the formula (I):

(I)

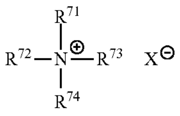

wherein two of $R^{71}$, $R^{72}$, $R^{73}$ and $R^{74}$ are selected from an aliphatic group of from 12 to 30 carbon atoms, preferably from 16 to 24 carbon atoms, more preferably from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Such preferred di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Mono-Long Alkyl Amine

Mono-long alkyl amine useful herein are those having one long alkyl chain of preferably from 12 to 30 carbon atoms, more preferably from 16 to 24 carbon atoms, still more preferably from 18 to 22 alkyl group. Mono-long alkyl amines useful herein also include mono-long alkyl amidoamines. Primary, secondary, and tertiary fatty amines are useful.

Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines are used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid, at a molar ratio of the amine to the acid of from about 1:0.3 to about 1:2, more preferably from about 1:0.4 to about 1:1.

High Melting Point Fatty Compound

The high melting point fatty compound useful herein have a melting point of 25° C. or higher, preferably 40° C. or higher, more preferably 45° C. or higher, still more preferably 50° C. or higher, in view of stability of the emulsion especially the gel matrix. Preferably, such melting point is up to about 90° C., more preferably up to about 80° C., still more preferably up to about 70° C., even more preferably up to about 65° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols.

Preferred fatty alcohols include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

In the present invention, more preferred fatty alcohol is a mixture of cetyl alcohol and stearyl alcohol.

Generally, in the mixture, the weight ratio of cetyl alcohol to stearyl alcohol is preferably from about 1:9 to 9:1, more preferably from about 1:4 to about 4:1, still more preferably from about 1:2.3 to about 1.5:1.

Silicone Compound

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

In some embodiments, amino substituted silicones are preferably used. Preferred aminosilicones include, for example, those which conform to the general formula (I):

$$(R_1)_aG_{3-a}\text{-Si—(—OSiG}_2)_n\text{-(—OSiG}_b(R_1)_{2-b})_m\text{—O—SiG}_{3-a}(R_1)_a$$

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: $—N(R_2)CH_2—CH_2—N(R_2)_2$; $—N(R_2)_2$; $—N(R_2)_3A^-$; $—N(R_2)CH_2—CH_2—NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Highly preferred amino silicones are those corresponding to formula (I) wherein m=0, a=1, q=3, G=methyl, n is preferably from about 1500 to about 1700, more preferably about 1600; and L is $—N(CH_3)_2$ or $—NH_2$, more preferably $—NH_2$. Another highly preferred amino silicones are those corresponding to formula (I) wherein m=0, a=1, q=3, G=methyl, n is preferably from about 400 to about 600, more preferably about 500; and L is $—N(CH_3)_2$ or $—NH_2$, more preferably $—NH_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as “amodimethicone”. Commercially available amodimethicones useful herein include, for example, BY16-872 available from Dow Corning.

Silicone Polymer Containing Quaternary Groups

Silicone compounds useful herein include, for example, a Silicone Polymer Containing Quaternary Groups comprising terminal ester groups, having a viscosity up to 100,000 mPa·s and a D block length of greater than 200 D units. Without being bound by theory, this low viscosity silicone polymer provides improved conditioning benefits such as smooth feel, reduced friction, and prevention of hair damage, while eliminating the need for a silicone blend.

Structurally, the silicone polymer is a polyorganosiloxane compound comprising one or more quaternary ammonium groups, at least one silicone block comprising greater than 200 siloxane units, at least one polyalkylene oxide structural unit, and at least one terminal ester group. In one or more embodiments, the silicone block may comprise between 300 to 500 siloxane units.

The silicone polymer is present in an amount of from about 0.05% to about 15%, preferably from about 0.1% to about 10%, more preferably from about 0.15% to about 5%, and even more preferably from about 0.2% to about 4% by weight of the composition.

In a preferred embodiment, the polyorganosiloxane compounds have the general formulas (Ia) and (Ib):

$$M\text{-}Y—[—(N^+R_2\text{-}T\text{-}N^+R_2)—Y—]_m—[—(NR^2\text{-}A\text{-}E\text{-}A'\text{-}NR^2)—Y\text{-}]_k\text{-}M \quad \text{(Ia)}$$

$$M\text{-}Y—[—(N^+R_2\text{-}T\text{-}N^+R_2)—Y—]_m—[—(N^+R^2{}_2\text{-}A\text{-}E\text{-}A'\text{-}N^+R^2{}_2)—Y\text{-}]_k\text{-}M \quad \text{(Ib)}$$

wherein:

m is >0, preferred 0.01 to 100, more preferred 0.1 to 100, even more preferred 1 to 100, specifically 1 to 50, more specifically 1 to 20, even more specifically 1 to 10, k is 0 or an average value of from >0 to 50, or preferably from 1 to 20, or even more preferably from 1 to 10, M represents a terminal group, comprising terminal ester groups selected from

—OC(O)—Z $—OS(O)_2—Z$ $—OS(O_2)O—Z$

—OP(O)(O—Z)OH $—OP(O)(O—Z)_2$ wherein Z is selected from monovalent organic residues having up to 40 carbon atoms, optionally comprising one or more hetero atoms.

A and A' each are independently from each other selected from a single bond or a divalent organic group having up to 10 carbon atoms and one or more hetero atoms, and E is a polyalkylene oxide group of the general formula:

$$—[CH_2CH_2O]_q—[CH_2CH(CH_3)O]_r—[CH_2CH(C_2H_5)O]_s—$$

wherein q=0 to 200, r=0 to 200, s=0 to 200, and q+r+s=1 to 600.

$R^2$ is selected from hydrogen or R,

R is selected from monovalent organic groups having up to 22 carbon atoms and optionally one or more heteroatoms, and wherein the free valencies at the nitrogen atoms are bound to carbon atoms, Y is a group of the formula:

—K—S—K— and —A—E—A'— or

—A'—E—A—, with S =

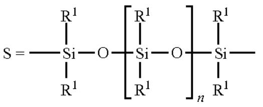

wherein $R1=C_1\text{-}C_{22}$-alkyl, $C_1\text{-}C_{22}$-fluoralkyl or aryl; n=200 to 1000, and these can be identical or different if several S Groups are present in the polyorganosiloxane compound.

K is a bivalent or trivalent straight chain, cyclic and/or branched $C_2\text{-}C_{40}$ hydrocarbon residue which is optionally interrupted by —O—, —NH—, trivalent N, $—NR^1—$, —C(O)—, —C(S)—, and optionally substituted with —OH, wherein $R^1$ is defined as above, T is selected from a divalent organic group having up to 20 carbon atoms and one or more hetero atoms.

The residues K may be identical or different from each other. In the K—S—K— moiety, the residue K is bound to the silicon atom of the residue S via a C—Si-bond.

Due to the possible presence of amine groups $(—(NR^2\text{-}A\text{-}E\text{-}A'\text{-}NR^2)—)$ in the polyorganosiloxane compounds, they may have protonated ammonium groups, resulting from the protonation of such amine groups with organic or inorganic acids. Such compounds are sometimes referred to as acid addition salts of the polyorganosiloxane compounds.

In a preferred embodiment the molar ratio of the quaternary ammonium groups b) and the terminal ester groups c) is less than 100:20, even more preferred is less than 100:30 and is most preferred less than 100:50. The ratio can be determined by $^{13}C$-NMR.

In a further embodiment, the polyorganosiloxane composition may comprise:

A) at least one polyorganosiloxane compound, comprising a) at least one polyorganosiloxane group, b) at least one quaternary ammonium group, c) at least one terminal ester group, and d) at least one polyalkylene oxide group (as defined before), B) at least one polyorganosiloxane compound, comprising at least one terminal ester group, different from compound A).

In the definition of component A) it can be referred to the description of the polyorganosiloxane compounds of the invention. The polyorganosiloxane compound B) differs from the polyorganosiloxane compound A) preferably in that it does not comprise quaternary ammonium groups. Preferred polyorganosiloxane compounds B) result from the reaction of monofunctional organic acids, in particular carboxylic acids, and polyorganosiloxane containing bisepoxides.

In the polyorganosiloxane compositions the weight ratio of compound A) to compound B) is preferably less than 90:10. Or in other words, the content of component B) is at least 10 weight percent. In a further preferred embodiment of the polyorganosiloxane compositions in compound A) the molar ratio of the quaternary ammonium groups b) and the terminal ester groups c) is less than 100:10, even more preferred is less than 100:15 and is most preferred less than 100:20.

The silicone polymer has a viscosity at 20° C. and a shear rate of 0.1 $s^{-1}$ (plate-plate system, plate diameter 40 mm, gap width 0.5 mm) of less than 100,000 mPa·s (100 Pa·s). In further embodiments, the viscosities of the neat silicone polymers may range from 500 to 100,000 mPa·s, or preferably from 500 to 70,000 mPa·s, or more preferably from 500 to 50,000 mPa·s, or even more preferably from 500 to 20,000 mPa·s. In further embodiments, the viscosities of the neat polymers may range from 500 to 10,000 mPa·s, or preferably 500 to 5000 mPa·s determined at 20° C. and a shear rate of 0.1 $s^{-1}$.

In addition to the above listed silicone polymers, the following preferred compositions are provided below. For example, in the polyalkylene oxide group E of the general formula:

$$—[CH_2CH_2O]_q—[CH_2CH(CH_3)O]_r—[CH_2CH(C_2H_5)O]_s—$$

wherein the q, r, and s indices may be defined as follows:

q=0 to 200, or preferably from 0 to 100, or more preferably from 0 to 50, or even more preferably from 0 to 20, r=0 to 200, or preferably from 0 to 100, or more preferably from 0 to 50, or even more preferably from 0 to 20, s=0 to 200, or preferably from 0 to 100, or more preferably from 0 to 50, or even more preferably from 0 to 20, and q+r+s=1 to 600, or preferably from 1 to 100, or more preferably from 1 to 50, or even more preferably from 1 to 40.

For polyorganosiloxane structural units with the general formula S:

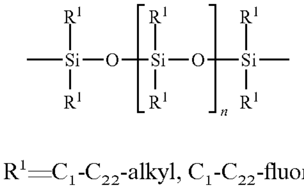

$R^1$=$C_1$-$C_{22}$-alkyl, $C_1$-$C_{22}$-fluoralkyl or aryl; n=from 200 to 1000, or preferably from 300 to 500, K (in the group —K—S—K—) is preferably a bivalent or trivalent straight chain, cyclical or branched $C_2$-$C_{20}$ hydrocarbon residue which is optionally interrupted by —O—, —NH—, trivalent N, —$NR^1$—, —C(O)—, —C(S)—, and optionally substituted with —OH.

In specific embodiments, $R^1$ is $C_1$-$C_{18}$ alkyl, $C_1$-$C_{18}$ fluoroalkyl and aryl. Furthermore, $R^1$ is preferably $C_1$-$C_{18}$ alkyl, $C_1$-$C_6$fluoroalkyl and aryl. Furthermore, $R^1$ is more preferably $C_1$-$C_6$ alkyl, $C_1$-$C_6$ fluoroalkyl, even more preferably $C_1$-$C_4$ fluoroalkyl, and phenyl. Most preferably, $R^1$ is methyl, ethyl, trifluoropropyl and phenyl.

As used herein, the term "$C_1$-$C_{22}$alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "$C_1$-$C_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples.

Moreover, the term "aryl" means unsubstituted or phenyl substituted once or several times with OH, F, Cl, $CF_3$, $C_1$-$C_6$ alkyl, $C_1$-$C_6$ alkoxy, $C_3$-$C_7$ cycloalkyl, $C_2$-$C_6$ alkenyl or phenyl. Aryl may also mean naphthyl.

For the embodiments of the polyorganosiloxanes, the positive charges resulting from the ammonium group(s), are neutralized with inorganic anions such as chloride, bromide, hydrogen sulfate, sulfate, or organic anions, like carboxylates deriving from $C_1$-$C_{30}$ carboxylic acids, for example acetate, propionate, octanoate, especially from $C_{10}$-$C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The quaternary ammonium groups are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

In a preferred embodiment the polyorganosiloxane compounds are of the general formulas (Ia) and (Tb):

$$M\text{-}Y—[—(N^+R_2\text{-}T\text{-}N^+R_2)—Y—]_m—[—(NR^2\text{-}A\text{-}E\text{-}A'\text{-}NR^2)—Y\text{-}]_k\text{-}M \quad (Ia)$$

$$M\text{-}Y—[—(N^+R_2\text{-}T\text{-}N^+R_2)—Y—]_m—[—(N^+R^2{}_2\text{-}A\text{-}E\text{-}A'\text{-}N^+R^2{}_2)—Y\text{-}]_k\text{-}M \quad (Ib)$$

wherein each group is as defined above; however, the repeating units are in a statistical arrangement (i.e., not a block-wise arrangement).

In a further preferred embodiment, the polyorganosiloxane compounds may be also of the general formulas (IIa) or (IIb):

$$M\text{-}Y—[—N^+R_2—Y—)]_m—[—(NR^2\text{-}A\text{-}E\text{-}A'\text{-}NR^2)—Y\text{-}]_k\text{-}M \quad (IIa)$$

$$M\text{-}Y—[—N^+R_2—Y—)]_m—[—(NR^2{}_2\text{-}A\text{-}E\text{-}A'\text{-}N^+R^2{}_2)—Y\text{-}]_k\text{-}M \quad (IIa)$$

wherein each group is as defined above. Also in such formula, the repeating units are usually in a statistical arrangement (i.e. not a block-wise arrangement).

wherein, as defined above, M is

—OC(O)—Z,

—OS(O)$_2$—Z

—OS(O$_2$)O—Z

—OP(O)(O—Z)OH

—OP(O)(O—Z)$_2$

Z is a straight chain, cyclic or branched saturated or unsaturated $C_1$-$C_{20}$, or preferably $C_2$ to $C_{18}$, or even more preferably a hydrocarbon radical, which can be interrupted by one or more —O—, or —C(O)— and substituted with OH. In a specific embodiment, M is —OC(O)—Z resulting from normal carboxylic acids in particular with more than 10 carbon atoms like for example dodecanoic acid.

In a further embodiment, the molar ratio of the polyorganosiloxane-containing repeating group K—S—K— and the polyalkylene repeating group -A-E-A'- or -A'-E-A- is between 100:1 and 1:100, or preferably between 20:1 and 1:20, or more preferably between 10:1 and 1:10.

In the group ($N^+R_2$-T-$N^+R_2$)—, R may represent a monovalent straight chain, cyclic or branched $C_1$-$C_{20}$ hydrocarbon radical, which can be interrupted by one or more —O—, —C(O)— and can be substituted by —OH, T may represent a divalent straight-chain, cyclic, or branched $C_1$-$C_{20}$ hydrocarbon radical, which can be interrupted by —O—, —C(O)— and can be substituted by hydroxyl.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters. Exemplary embodiments include $C_1$-$C_{30}$ carboxylic acids, for example $C_2$, $C_3$, $C_8$ acids, $C_{10}$-$C_{18}$ carboxylic acids, for example $C_{12}$, $C_{14}$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Additional Components

The personal care composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; perfumes; ultraviolet and infrared screening and absorbing agents such as benzophenones; and antidandruff agents such as zinc pyrithione.

Preparation of Solid Discrete Particle and Mixture Composition

The mixture composition is prepared by steps of:

preparing a melting mixture composition comprising the surfactant and the high melting point fatty compound, wherein the temperature of the melting mixture composition is higher than the melting point of the high melting point fatty compound contained in the mixture composition;

cooling the melting mixture composition to a temperature which is lower than the melting point of the high melting point fatty compound contained in the mixture composition, to form the mixture composition. The discrete particle can be prepared concurrently when preparing the mixture composition during the above cooling step, or can be prepared after forming the mixture composition.

Preferably, the temperature of the melting mixture composition is at least 2° C., still more preferably at least 5° C., even more preferably at least 10° C. higher than the above melting point of the high melting point fatty compound. It is also preferred that the temperature of the melting mixture composition is from about 30° C. to about 150° C., more preferably from about 40° C. to about 100° C., still more preferably from about 50° C. to about 95° C., even more preferably from about 55° C. to about 90° C., further more preferably from about 66° C. to about 90° C.

Preferably, the melting mixture composition is cooled to a temperature which is lower than a melting point of the high melting point fatty compound contained in the mixture composition, more preferably at least 2° C., more preferably at least 5° C., still more preferably at least 10° C. lower than the melting point of the high melting point fatty compound contained in the mixture composition. It is also preferred that the melting mixture composition is cooled to a temperature of from about −200° C. to about 50° C., more preferably from about −40° C. to about 50° C., still more preferably from about 0° C. to about 30° C.

When Containing the Benefit Agents in the Mixture Composition

When the mixture composition further comprises the benefit agents, the mixture composition can be prepared by steps of:

Preparing a melting mixture composition comprising the surfactant and the high melting point fatty compound, wherein the temperature of the melting mixture composition is higher than a melting point of the high melting point fatty compound contained in the mixture composition;

cooling the melting mixture composition to the temperature which is lower than a melting point of the high melting point fatty compound contained in the mixture composition, to form the mixture composition, wherein the benefit agent can be added anytime depending on the properties of the benefit agent, for example, the benefit agent can be added to the mixture composition before cooling, during cooling especially when using volatile benefit agent such as perfumes, or after cooling preferably right after cooling such as within 30 min after cooling.

When the mixture composition comprises a benefit agent, the benefit agent can be homogeneously mixed with the mixture composition, and homogeneous discrete particles can be formed in the compositions.

Alternatively, in the discrete particle, the benefit agent can form an inner core covered by an outer shell formed by the mixture composition.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Customized Product Compositions—R

| | | Wt % in the customized product composition | | | |
|---|---|---|---|---|---|
| | | Ex. R-1 | Ex. R-2 | Ex. R-3 | Ex. R-4 |
| Aqueous hair care composition | BTMS/IPA *1 | 2.4 | 1.2 | 3.57 | — |
| | Stearamidopropyl Dimethylamine | — | — | — | 0.95 |
| | L-Glutamic acid | — | — | — | 0.34 |
| | Cetyl Alcohol | 0.8 | 0.4 | 1.2 | 0.8 |
| | Stearyl alcohol | 2.0 | 1.0 | 3.0 | 1.4 |
| | Disodium EDTA | 0.1 | 0.05 | 0.13 | 0.07 |
| | Benzyl Alcohol | 0.3 | 0.16 | 0.5 | 0.2 |
| | Kathon CG | 0.02 | 0.01 | — | — |
| | Aminosilicone *2 | — | 0.45 | — | — |
| | Water | q.s. to 100% | q.s. to 100% | q.s. to 100% | q.s. to 100% |
| Solid discrete particles of Mixture composition | Mixture composition having the following composition | 1.37 | 4.12 | — | — |
| | Wt % in the mixture composition | | | | |
| | BTMS/IPA *1 45.6 | | | | |
| | Cetyl Alcohol 15.5 | | | | |
| | Stearyl alcohol 38.9 | | | | |
| Solid discrete particles of Mixture composition - 2 | Mixture composition having the following composition | — | — | 6.5 | 3.5 |
| | Wt % in the mixture composition | | | | |
| | Stearamidopropyl Dimethylamine 45.5 | | | | |
| | Cetyl Alcohol 15.6 | | | | |
| | Stearyl alcohol 38.9 | | | | |
| Particle size of Discrete particle, before mixing with the aqueous hair care composition | | 200-300 microns | 0.6 mm | 100 microns | 1000 microns |
| Benefit | | The customized hair care product compositions containing discrete particles provide at least one of the following benefits, compared to those without discrete particles: Boosting rhelology and/or boosting rich conditioning perception/feeling; Boosting conditioning benefit; | | | |

Customized Product Compositions—S

| | | Wt % in the customized product composition | |
|---|---|---|---|
| | | Ex. S-1 | Ex. S-2 |
| Aqueous Hair care composition | Cetyl alcohol | 0.4 | 0.4 |
| | Stearyl alcohol | 1.0 | 1.0 |
| | BTMS/IPA *1 | 1.2 | 1.2 |
| | Disodium EDTA | 0.05 | 0.05 |
| | Benzyl Alcohol | 0.16 | 0.16 |
| | Kathon CG | 0.01 | 0.01 |
| | Water | q.s. to 100% | q.s. to 100% |
| Solid discrete particles of Mixture composition-1 | Mixture composition including Aminosilicone*2, having the following composition: | 4.54 | — |
| | (wt % in the mixture composition) | | |

-continued

| | | Wt % in the customized product composition | |
|---|---|---|---|
| | | Ex. S-1 | Ex. S-2 |
| | Cetyl alcohol 14.0<br>Stearyl alcohol 35.0<br>BTMS/IPA *1 41.0<br>Aminosilicone *2 10.0 | | |
| Solid discrete particles of Mixture composition-2 | Mixture composition including Quaternized aminosilione *3 having the following composition<br>(wt % in the mixture composition)<br>Cetyl alcohol 14.0<br>Stearyl alcohol 35.0<br>BTMS/IPA *1 41.0<br>Quaternized aminosilione *3 10.0 | — | 4.54 |
| Particle size of Discrete particle, before mixing with the aqueous hair care composition | | 300-500 micrometer | |
| Benefit | | The customized hair care product compositions containing discrete particles provide at least one of the following benefits, compared to those without discrete particles:<br>Boosting rhelology and/or boosting rich conditioning perception/feeling;<br>Boosting conditioning benefit; | |

Customized Product Composition—M

| | | Wt % in the customized product composition | |
|---|---|---|---|
| | | Ex. M-1 | CEx. M-i |
| Aqueous hair care composition | Cetyl alcohol | 1.2 | 1.2 |
| | Stearyl alcohol | 3.0 | 3.0 |
| | BTMS/IPA *1 | 2.2 | 2.2 |
| | Dicetyl dimethyl Ammonium Chloride | 0.5 | 0.5 |
| | Disodium EDTA | 0.13 | 0.13 |
| | Benzyl Alcohol | 0.4 | 0.4 |
| | Kathon CG | 0.03 | 0.03 |
| | Water | q.s. to 100% | q.s. to 100% |
| | Aminosilicone *2 | 1.5 | 1.5 |
| | Mica | — | 0.24 |
| Solid discrete particles of Mixture composition | Mixture composition including mica, having the following composition<br>(w % in the mixture composition)<br>Cetyl alcohol 11.7<br>Stearyl alcohol 29.1<br>BTMS/IPA *1 34.1<br>Mica 25.1 | 3.84 | — |
| Particle size of Discrete particle, before mixing with the aqueous hair care composition | | 200-300 micrometers | n/a |
| Agglomeration/Residue | | Significant reduction of mica agglomeration compared to CEx. M-i. Almost no visible mica agglomeration is observed in the customized product composition even after 18 months. | Visible mica agglomerations are observed in the product composition |

Customized Product Compositions—P

| | | Wt % in the customized product composition | |
|---|---|---|---|
| | | Ex. P-1 | Ex. P-2 |
| Aqueous Hair care composition | Cetyl alcohol | 1.0 | 1.0 |
| | Stearyl alcohol | 2.5 | 2.5 |
| | BTMS/IPA *1 | 3.0 | 3.0 |
| | Disodium EDTA | 0.13 | 0.13 |
| | Benzyl Alcohol | 0.4 | 0.4 |
| | Kathon CG | 0.03 | 0.03 |
| | Water | q.s. to 100% | q.s. to 100% |
| | Green Dye (mixture of Blue 1 + Yellow 5 + DI water) | — | 0.8 |
| Solid discrete particle of Mixture composition-1 | Mixture composition including Red pigment, having the following composition (w % in the mixture composition) | 0.4 | — |
| | Cetyl alcohol 15.5 | | |
| | Stearyl alcohol 38.5 | | |
| | BTMS/IPA *1 45.0 | | |
| | Pigment (OTS-2-RED-516P) 1 | | |
| Solid discrete particle of Mixture composition-2 | Mixture composition including Black pigment, having the following composition (w % in the mixture composition) | — | 0.2 |
| | Cetyl alcohol 15.5 | | |
| | Stearyl alcohol 38.5 | | |
| | BTMS/IPA *1 45.0 | | |
| | Pigment (OTS-2-BLACK-BL100P) 1 | | |
| Particle size of Discrete particle, before mixing with the aqueous hair care composition | | 300-500 mictometers | |
| Aesthetics | | The discrete particles are observed in the customized product composition as red-colored dispersions | The discrete particles are observed in the customized product composition as black-colored dispersions |

Customized Product Compositions—SA

| | | Wt % in the customized product composition | | |
|---|---|---|---|---|
| | | Ex. SA-1 | Ex. SA-2 | CEx. SA-i |
| Aqueous Hair care composition | Cetyl alcohol | 0.38 | 0.38 | 1.2 |
| | Stearyl alcohol | 0.9 | 0.9 | 3.0 |
| | BTMS/IPA *1 | 0.96 | 0.96 | 3.0 |
| | Disodium EDTA | 0.04 | 0.04 | 0.17 |
| | Benzyl Alcohol | 0.13 | 0.13 | 0.4 |
| | Kathon CG | 0.01 | 0.01 | 0.03 |
| | Water | q.s. to 100% | q.s. to 100% | q.s. to 100% |
| | Salicylic acid | — | — | 2.0 |
| | Quaternized aminosilione *3 | — | — | 3.5 |
| Solid discrete particles of Mixture composition -1 | Mixture composition including Salicylic acid, having the following composition: (wt % in the mixture composition) | 17.8 | — | — |
| | Cetyl alcohol 28.9 | | | |
| | Stearyl alcohol 19.9 | | | |
| | BTMS/IPA *1 17.7 | | | |
| | Stearamidopropyl Dimethylamine 11.0 | | | |
| | Salicylic acid 22.5 | | | |
| Solid discrete particles of | Mixture composition including Salicylic acid, having the following composition | — | 13.4 | — |

-continued

| | | | Wt % in the customized product composition | | |
|---|---|---|---|---|---|
| | | | Ex. SA-1 | Ex. SA-2 | CEx. SA-i |
| Mixture composition -2 | | (wt % in the mixture composition) | | | |
| | Cetyl alcohol | 26.0 | | | |
| | Stearyl alcohol | 18.0 | | | |
| | BTMS/IPA *1 | 16.0 | | | |
| | Stearamidopropyl Dimethylamine | 10.0 | | | |
| | Salicylic acid | 30.0 | | | |
| Particle size of Discrete particle, before mixing with the aqueous hair care composition | | | 1.2 mm | | n/a |
| Crystallization | | | No needle like crystallization of Salicylic acid is observed in the customized product composition even after 3 months | | Needle like crystallization of Salicylic acid is observed in the product composition |

Customized Product Compositions—CEx.

| | | | Wt % in the customized product composition CEx. i |
|---|---|---|---|
| Aqueous composition | Water | | q.s. to 100% |
| Solid discrete particles of Mixture composition | Mixture composition having the following composition | | 6.86 |
| | | Wt % in the mixture composition | |
| | BTMS/IPA *1 | 45.6 | |
| | Cetyl Alcohol | 15.5 | |
| | Stearyl alcohol | 38.9 | |
| Particle size of Discrete particle, before mixing with the aqueous composition | | | 1 mm |

Customized Product Compositions—RP

| | | | Wt % in the customized product composition | |
|---|---|---|---|---|
| | | | Ex. RP-1 | Ex. RP-2 |
| Aqueous composition | Water soluble polymer-1*4 | | 1.5 | |
| | Water soluble polymer-2 *5 | | | 0.4 |
| | Water | | q.s. to 100% | q.s. to 100% |
| Solid discrete particles of Mixture composition | Mixture composition having the following composition | | 6.86 | 12.5 |
| | | Wt % in the mixture composition | | |
| | BTMS/IPA *1 | 45.6 | | |
| | Cetyl Alcohol | 15.5 | | |
| | Stearyl alcohol | 38.9 | | |
| Particle size of Discrete particle, before mixing with the aqueous composition | | | 1 mm | 10 mm |
| Benefit | | | The customized hair care product compositions containing discrete particles provide at least one of the following benefits, compared to those without discrete particles: Boosting rhelology and/or boosting rich conditioning perception/feeling; Boosting conditioning benefit; | |

Definitions of Components

1 BTMS/IPA: 80% of Behenyl Trimethyl Ammonium Methosulfate and 20% of Isopropyl alcohol 2 Aminosilicone: Available from Momentive having a viscosity 10,000 mPa·s, and having following formula (I):

$$(R_1)_aG_{3-a}\text{-Si—(—OSiG}_2)_n\text{-(—OSiG}_b(R_1)_{2-b})_m\text{—O—SiG}_{3-a}(R_1)_a \qquad (I)$$

wherein G is methyl; a is an integer of 1; b is 0, 1 or 2, preferably 1; n is a number from 400 to about 600; m is an integer of 0; $R_1$ is a monovalent radical conforming to the general formula $CqH_{2q}L$, wherein q is an integer of 3 and L is —$NH_2$ 3 Quaternized aminosilione: Available from Momentive having the following formula:

$$M\text{-}Y—[—(N^+R_2\text{-}T\text{-}N^+R_2)—Y—]_m—[—(N^+R^2_2\text{-}A\text{-}E\text{-}A'\text{-}N^+R^2_2)—Y\text{-}]_k\text{-}M$$

wherein

| | |
|---|---|
| M | lauric ester |
| Y | K—S—K |
| K | $CH_2$—CHOH—$CH_2$—O—$C_3H_6$ |
| S | PDMS block with 368 siloxane units |
| R, $R^2$ | Methyl |
| T | $C_6H_{12}$ |
| A | $CH_2$—COO— |
| A' | CO—$CH_2$ |
| E | Ethylene oxide ($CH_2$—$CH_2$—O) with average degree of ethoxylation of 2 |
| Ratio of silicone blocks:alkylene oxide blocks | 1:1 |
| Total Viscosity | 4700 mPa · s |

* 4 Water soluble polymer-1: ADEKA NOL GT-730 supplied from Adeka (30% of PEG-240/HDI COPOLYMER BIS-DECYLTETRADECETH-20 ETHER, 50% of butylene glycol, and 20% of water)

*5 Water soluble polymer-2: Polyquaternium-37

Method of Preparation of the Customized Product Composition

The embodiments disclosed and represented by "Ex." are customized personal care product compositions of the present invention, and were prepared and applied by the usage instruction comprising depiction corresponding to the following steps:

(i) mixing an aqueous personal care composition and the solid discrete particles at room temperature to make a customized personal care product; and (ii) applying the customized personal care product to the target surface.

The solid discrete particles were prepared by the following method:

Preparing a melting mixture composition wherein the temperature of the melting mixture composition is higher than a melting point of the high melting point fatty compound contained in the mixture composition, i.e., from about 66° C. to about 90° C.;

Cooling the melting mixture composition to a temperature which is lower than a melting point of the high melting point fatty compound contained in the mixture composition, i.e., from about 0° C. to about 40° C., to form the mixture composition; and Preparing a solid discrete particle consisting of the mixture composition.

The solid discrete particles were contained in a container separated from the personal care composition before mixing, and the above usage instruction is attached to the container.

The personal care product compositions disclosed and represented by "CEx." are comparative examples, and were prepared by the above method for those with solid discrete particles, or by a conventional method for those without solid discrete particles.

Properties and Benefits

The embodiments disclosed and represented by "Ex." are customized personal care product compositions of the present invention which are particularly useful for rinse-off use, and have many advantages. For example, the present invention provides at least one the followings:

Boosting rheology especially storage modulus (G') and/or boosting rich conditioning perception/feeling, preferably independently from the use of thickening polymer.

Boosting conditioning benefits

Adding a new benefit such as aesthetic benefit, anti-dandruff benefit, sensate such as heating/cooling, and scent Providing at least one of the above benefits, while having improved stability especially when containing incompatible components and/or while not causing negative interaction with personal care composition, package, and any other environmental factors.

Some of such benefits may be understood by the comparison with comparative examples "CEx.".

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A solid, discrete hair conditioning particle, comprising:

a) a cationic surfactant selected from the group consisting of mono-long alkyl quaternized ammonium salt, a combination of mono-long alkyl quaternized ammonium salt and di-long alkyl quaternized ammonium salt, mono-long alkyl amine, and a combination of mono-long alkyl amine and di-long alkyl quaternized ammonium salt;

b) a high melting point fatty compound selected from the group consisting of fatty alcohols, fatty acids, fatty alcohol derivatives, fatty acid derivatives, and mixtures thereof; and c) a benefit agent selected from the group consisting of silicone compounds, perfumes, aesthetic benefit agents, sensate agents, anti-dandruff agents, incompatible agents and mixtures thereof, wherein the hair conditioning particle has a particle size of 50 micrometers to about 2000 micrometers.

2. The particle of claim 1, further comprising less than about 25% water, based on the weight of the particle.

3. The particle of claim 2, further comprising less than about 10% water, based on the weight of the particle.

4. The particle of claim 1, wherein the cationic surfactant and high melting point fatty alcohol are present at about 40% to about 100%, based on the weight of the particle.

5. The particle of claim 1, wherein the cationic surfactant and the high melting point fatty compound are present at a weight ratio of surfactant to high melting point fatty compound of about 1:1 to about 1:10.

6. The particle of claim 1, wherein the high melting point fatty compound has a melting point of 40° C. or higher.

7. The particle of claim 6, wherein the high melting point fatty compound is chosen from stearyl alcohol, cetyl alcohol and behenyl alcohol, and mixtures thereof.

8. The particle of claim 1, wherein the particle is not coated or encapsulated.

9. The particle of claim 1, wherein the particle contains less than 50% liquid.

10. The particle of claim 1, wherein the benefit agent is a aesthetic benefit agent that imparts a color to the particle.

11. The particle of claim 1, further comprising a swellable thickening polymer chosen from polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, polyurethanes, polycarboxylic acids, polyvinyl acetates, polyesters, polyamides, polyamines, polyethyleneimines and combinations thereof.

12. The particle of claim 1, further comprising liquid polypropylene glycol.

13. The particle of claim 1, wherein the particle is free of swellable silicone elastomer.

14. A method of making a hair conditioning product, comprising: mixing a multitude of particles of claim 1 with an aqueous carrier such that the particles are dispersed in the aqueous carrier to form the hair conditioning product.

15. The method of claim 14, wherein the hair conditioning product is free of a detersive surfactant selected from the group consisting of anionic surf actant, zwitterionic surf actant, and amphoteric surfactant.

16. The method of claim 14, wherein the particles swell in the aqueous carrier.

17. The method of claim 16, wherein the swollen particles do not form an emulsion in the hair conditioning product.

* * * * *